US007618623B2

(12) United States Patent
Zheng et al.

(10) Patent No.: US 7,618,623 B2
(45) Date of Patent: *Nov. 17, 2009

(54) HYBRID ADENO-RETROVIRAL VECTOR FOR THE TRANSFECTION OF CELLS

(75) Inventors: Changyu Zheng, Rockville, MD (US); Brian O'Connell, Dublin (IE); Bruce J. Baum, Bethesda, MD (US)

(73) Assignee: The United of States of America as represented by the Secretary of the Department of Health and Human Services, Bethesda, MD (US)

( * ) Notice: Subject to any disclaimer, the term of this patent is extended or adjusted under 35 U.S.C. 154(b) by 364 days.

This patent is subject to a terminal disclaimer.

(21) Appl. No.: 11/255,059

(22) Filed: Oct. 19, 2005

(65) Prior Publication Data

US 2006/0035371 A1  Feb. 16, 2006

Related U.S. Application Data

(63) Continuation of application No. 10/182,644, filed as application No. PCT/US01/03026 on Jan. 30, 2001, now Pat. No. 7,052,904.

(60) Provisional application No. 60/179,327, filed on Jan. 31, 2000.

(51) Int. Cl.
| A61K 48/00 | (2006.01) |
| A01N 63/00 | (2006.01) |
| A01N 43/04 | (2006.01) |
| A61K 31/711 | (2006.01) |
| C12N 15/861 | (2006.01) |
| C12N 15/867 | (2006.01) |
| C12N 15/33 | (2006.01) |

(52) U.S. Cl. .................... 424/93.3; 424/93.1; 424/93.2; 424/93.6; 514/44; 435/456; 435/320.1

(58) Field of Classification Search ........................ None
See application file for complete search history.

(56) References Cited

U.S. PATENT DOCUMENTS

| 5,681,746 A | 10/1997 | Bodner et al. |
| 6,303,380 B1 | 10/2001 | Lin et al. |
| 2002/0150876 A1 | 10/2002 | Pippig et al. |

OTHER PUBLICATIONS

Zheng C. et al., "Long-Term Expression after Infection by the Hybrid Vector AdLTR-luc Is from Integrated Transgene", 2002, Biochem. Biophys. Res. Comm., vol. 291: pp. 34-40.*
Zheng, C. et al., "Inclusion of Moloney murine leukemia virus elements upstream of the transgene cassette in an E1-deleted adenovirus leads to an unusual genomic integration in epithelial cells", 2003, Virology, vol. 313: pp. 460-472.*
Graham, F. "Adenovirus Vectors for Gene Expression and Gene Therapy", 1996, Transfus. Sci., vol. 17: pp. 15-27.*
Takeuchi, M. et al., "Relationship between sugar chain structure and biological activity of recombinant human erythropoietin produced in Chinese hamster ovary cells", 1989, PNAS, vol. 86: pp. 7819-7822.*
Babincova et al., "Anaerobic bacteria as a luciferase gene delivery system for endogenous generation of photodynamic light inside tumors," *Life and Medical Sciences Online*, (2000), pp. 1-4.
Barry et al., "Glucose-Regulated Insulin Expression in Diabetic Rats," *Human Gene Therapy*, 12:131-139, 2001.
Basak et al., "Modifying Adenoviral Vectors for Use as Gene-Based Cancer Vaccines," *Viral Immunology*, 17(2):182-196, 2004.
Dang et al., "Gene Therapy and Translation Cancer Research," *Clinical Cancer Research*, 5:471-474, 1999.
Ratner et al., "Complete nucleotide sequence of the AIDS virus, HTLV-III," *Nature*, 313:277-284, 1985.
Sivak et al., "A Novel Intron Element Operates Posttranscriptionally To Regulate Human N-*myc* Expression," *Molecular and Cellular Biology*, 19(1):155-163, 1999.
Stone et al., "Viral vectors for gene delivery and gene therapy within the endocrine system," *Journal of Endocrinology*, 164:103-118, 2000.
Vanderwaak et al., "An Advanced Generation of Adenoviral Vectors Selectively Enhances Gene Transfer for Ovarian Cancer Gene Therapy Approaches," *Gynecologic Oncology*, 74:227-234, 1999.

* cited by examiner

*Primary Examiner*—Michael Burkhart
(74) *Attorney, Agent, or Firm*—Klarquist Sparkman, LLP.

(57) ABSTRACT

An adenovirus, including adenoviral capsid proteins, and a replication-defective adenoviral vector that includes a 5' retroviral LTR nucleic acid sequence, a 3' retroviral LTR nucleic acid sequence, a nucleic acid sequence encoding a portion of a retroviral envelope protein adjacent to either the 5' LTR or the 3' LTR nucleic acid sequence, a retroviral packaging sequence and a nucleic acid sequence encoding a transgene located between the 5' LTR and the 3' LTR is provided. Host cells infected with this adenovirus are also provided. An adenoviral vector is provided that includes an adenoviral polynucleotide sequence comprising a nucleic acid encoding a transgene, a retroviral packaging signal, a 5' and a 3' retroviral LTR, and a portion of a retroviral envelope polypeptide, wherein the adenoviral polynucleotide sequence does not encode one or more of E1, E3 or E4. A method for transforming a cell is also provided using a virus or a vector of the invention, as is a method for introducing a transgene into a cell that is not able to produce viral particles with a single viral vector. A method is also provided for preventing or treating disorder in a subject using the adenoviral vectors of the invention. A pharmaceutical composition is also provided that includes an adenoviral vector of the invention and a pharmaceutically acceptable carrier.

14 Claims, 14 Drawing Sheets

A. Dividing Cells

B. Non-Dividing

C. Submandibular Gland

D. Cortex

E. Caudate Nucleus

Diagram of PCR design to detect integration

Diagram of gene walking strategy to sequence virus-genomic DNA junction

FIG. 10

Sequence Range: 1 to 2726

| Enzyme | #Cuts | Positions | | | | | |
|---|---|---|---|---|---|---|---|
| AluI | 11 | 560 | 717 | 1167 | 1266 | 1270 | 1357 |
|  |  | 1432 | 1651 | 1894 | 1974 | 1982 |  |
| BstEII | 1 | 2409 |  |  |  |  |  |
| EcoRV | 4 | 1028 | 1124 | 1379 | 1454 |  |  |
| HaeIII | 21 | 3 | 301 | 379 | 534 | 572 | 625 |
|  |  | 697 | 824 | 925 | 1368 | 1413 | 1443 |
|  |  | 1488 | 1898 | 2032 | 2068 | 2080 | 2309 |
|  |  | 2433 | 2454 | 2519 |  |  |  |
| HincII | 3 | 317 | 617 | 971 |  |  |  |
| HinfI | 9 | 87 | 344 | 539 | 813 | 967 | 1149 |
|  |  | 1706 | 2089 | 2114 |  |  |  |
| KpnI | 3 | 260 | 443 | 1720 |  |  |  |
| MspI | 11 | 115 | 335 | 461 | 607 | 1403 | 1478 |
|  |  | 1713 | 1841 | 1883 | 2029 | 2723 |  |
| NcoI | 1 | 647 |  |  |  |  |  |
| PstI | 2 | 2251 | 2427 |  |  |  |  |
| PvuII | 3 | 1167 | 1357 | 1432 |  |  |  |
| SacI | 1 | 1653 |  |  |  |  |  |
| Sau3AI | 9 | 583 | 738 | 1003 | 1330 | 1844 | 2103 |
|  |  | 2366 | 2498 | 2683 |  |  |  |
| SmaI | 1 | 1714 |  |  |  |  |  |
| SpeI | 2 | 906 | 1966 |  |  |  |  |
| XbaI | 1 | 1533 |  |  |  |  |  |

FIG 11

Sequence Range: 1 to 1013

| Enzyme | #Cuts | Positions | | | | | |
|---|---|---|---|---|---|---|---|
| AluI | 11 | 19 | 99 | 198 | 202 | 289 | 364 |
|  |  | 583 | 826 | 906 | 914 | 1000 |  |
| EcoRI | 2 | 1 | 982 |  |  |  |  |
| EcoRV | 3 | 56 | 311 | 386 |  |  |  |
| HaeIII | 6 | 300 | 345 | 375 | 420 | 830 | 964 |
| HinfI | 2 | 81 | 638 |  |  |  |  |
| KpnI | 1 | 652 |  |  |  |  |  |
| MspI | 6 | 335 | 410 | 645 | 773 | 815 | 961 |
| PvuII | 3 | 99 | 289 | 364 |  |  |  |
| SacI | 1 | 585 |  |  |  |  |  |
| Sau3AI | 2 | 262 | 776 |  |  |  |  |
| SmaI | 1 | 646 |  |  |  |  |  |
| SpeI | 1 | 898 |  |  |  |  |  |
| XbaI | 1 | 465 |  |  |  |  |  |

Diagram of part of *Bam* HI
and *Not* I sites in AdLTR-luc.

.Partial diagram of *Sal* I and *Xho* I sites in AdLTR-luc.

Diagram of part of *Bgl* I and *Nco* I sites in AdLTR-luc.

Partial diagram of *Not* I sites in AdLTR-luc.

Partial diagram of *Bam* HI, *Xba* I, *Sac* I, *Kpn* I and *Nco* I sites in AdLTR-luc.

Diagram of PCR design to detect 3'LTR break

HYBRID ADENO-RETROVIRAL VECTOR FOR THE TRANSFECTION OF CELLS

PRIORITY CLAIM

This is a continuation of U.S. patent application Ser. No. 10/182,644, filed on Jul. 30, 2002, now U.S. Pat. No. 7,052,904, which is incorporated by reference herein in its entirety. U.S. patent application Ser. No. 10/182,644 is the §371 U.S. national stage of PCT/US01/03026, filed Jan. 30, 2001, which was published in English under PCT Article 21(2), and claims the benefit of U.S. Application No. 60/179,327, filed Jan. 31, 2000.

FIELD OF THE INVENTION

This invention relates to the field of viral vectors and the transduction of cells, more specifically to hybrid adenoviral vectors and their use in the transduction of cells in vitro or in vivo.

BACKGROUND

The transfer of genes into cells provides a means to determine gene function and treat diseases of genetic basis. In addition, gene transfer provides the basis for high-level protein expression, used by molecular researchers to study protein function and to produce new protein drugs. The introduction of genes into animals can also produce useful animal models of human diseases.

Many methods have been developed to introduce exogenous genes into cells. The earliest method for introducing DNA into cells was to incubate the DNA with an inert carbohydrate polymer (dextran) to which a positively charged chemical group (DEAE) had been coupled. These large DNA-containing particles stuck to cells and were taken up by endocytosis. However, this method was inefficient for the introduction of nucleic acid into many types of cells. Another widely used method is the precipitation of DNA with calcium phosphate, which allows transient expression of genes in cells. However, neither of these methods allow the transfer of nucleic acids into a cell with a high efficiency, nor do they allow for persistent gene expression. Thus, a need remains for a high efficiency method for the stable introduction of genes into cells.

Viral vectors, such as adenoviral or retroviral vectors, have been used to introduce foreign DNA with high efficiency. These vectors include adenoviral vectors and retroviral vectors.

The wild type adenovirus genome is approximately 36 kb, of which up to 30 kb can be replaced with foreign DNA. There are four early transcriptional units (E1, E2, E3 and E4), which have regulatory functions, and a late transcript, which codes for structural proteins. Replication-defective vectors have been produced, which have an essential region of the virus (e.g. E1) deleted. Other genes (e.g. E3 or E4) can be also deleted in the replication-deficient vectors. These additional gene deletions increase the capacity of the vector to carry exogenous nucleic acid sequences. The E2 region can also be deleted in a replication-defective vector; this type of vector is known as a "mini Ad," "gutted vector," or "gutless vector." In order to utilize these "gutless vectors", a helper cell line, (e.g. 293 cells), is needed to provide necessary proteins for virus packaging. Although adenoviral vectors, including gutless vectors, can infect both dividing and non-dividing cells, they generally do not stably integrate into the cellular genome.

In an alternative strategy, retroviruses, such as Moloney murine leukemia virus (MoMLV), have been used to introduce genes into cells. Retroviruses are RNA viruses that, when they infect cells, convert their RNA into a DNA form, which is then integrated into the cellular genome. The integrated provirus can produce RNA from a promoter located in the long terminal repeats (LTRs), which are DNA repeats located at the end of the integrated genome. Retroviral DNA vectors are plasmid DNAs which contain two retroviral LTRs, and a gene of interest inserted in the region internal to these LTRs. The retroviral vector can be packaged by packaging cell lines, containing the gag, pol, and env genes, which provide all the viral proteins required for capsid production and the virion maturation of the vector.

A retroviral vector integrates into the cellular genome once it is introduced into cells, thereby stably transfecting the cells. However, retroviruses can transform only cells that are dividing; retroviral vectors cannot be used to introduce nucleic acid into non-dividing cells.

Recently, hybrid virus expression systems have been developed, which are designed to improve gene transfer protocols where long-term expression is desired in both dividing and non-dividing cells (Duisit et al., Human Gene Therapy 10:189-200, 1999; Caplan et al, Gene Therapy 6:454-459, 1999; Lin, Gene Therapy 5: 1251-1258, 1998). However, since the recombinant vector produced is a retrovirus, cell division is still required for virus infection and integration. This latter fact is a significant drawback to target cells that are terminally differentiated and non-dividing. In addition, each of these systems requires the use of more than one virus. Thus a need remains for a single vector which provides high efficiency, stable transfection in vitro of both dividing and non-dividing cells, without requiring the presence of additional viruses or viral proteins.

The high-efficiency transfer of genes is also of use in vivo. Over the past decade a new approach to the treatment of disease has been developed using genes as therapeutic agents. The goal of gene therapy is to deliver DNA into the body for the treatment of an array of inherited and acquired diseases. Since the first clinical gene therapy protocol for severe combined immunodeficiency disease started in September 1990, more than 300 clinical protocols have been approved worldwide. Clinical experience suggests that gene therapy has the potential to treat a broad range of human diseases, with a low risk of adverse reactions. However, the efficiency of gene transfer and expression in vivo is still relatively low (Donehower, et al., Proc. Natl. Acad. Sci. USA 81: 6461-6465, 1984.

The gene delivery system is frequently the limiting factor for successful gene therapy. Ideally, a gene therapy vector should efficiently and safely deliver therapeutic genes to the target tissues, and should produce a therapeutic amount of gene product for the appropriate time, without requiring any complementing functions supplied in trans. Unfortunately, none of the vector systems presently in use meet all of these requirements.

Both retroviruses (e.g., Moloney Murine Leukemia Virus, MoMLV), and adenoviruses, have been used for human gene therapy. Experience has demonstrated that although a retroviral vector such as a MoMLV vector is a minimal safety risk, its low titer and low gene transfer efficiency make it most suitable for ex vivo use. In addition, as described above, MoMLV can integrate into the genome only in dividing cells.

In contrast to a retrovirus, the transport of an adenovirus to the nucleus is rapid in both dividing and non-dividing cells in vivo. However, an immune response can be generated against the adenoviral proteins produced by an adenoviral vector. In general, the "gutless vectors" induce less of an immune response than other adenoviral vectors. Although adenoviruses can be produced at very high titers and may infect cells with high efficiency, they integrate into the cell genome only at very low frequency, which results in unstable gene expression.

Thus a need exists for a single vector which can be used to stably introduce nucleic acid into both dividing and nondividing cells, which can be used both in vitro and in vivo.

SUMMARY OF THE INVENTION

A hybrid adenovirus is provided, which has the ability to integrate into genomic DNA and to mediate long term gene expression by stably transforming a host cell. The use of the hybrid vectors of the invention does not require the production of viral particles by the host cell. In addition, the method of transfecting cells with the hybrid adenoviral vector of the invention does not require the use of additional vectors to provide functions in trans. The hybrid adenoviral vectors of the invention can be used to transfect host cells in vitro, or can be used to deliver nucleic acid sequences in vivo. The hybrid adenovirus can be introduced into either dividing or non-dividing cells.

An adenovirus is provided that includes adenoviral capsid proteins, and a replication-defective adenoviral vector. The replication-defective adenoviral vector includes a 5' retroviral LTR nucleic acid sequence, a 3' retroviral LTR nucleic acid sequence, a nucleic acid sequence encoding a portion of a retroviral envelope protein adjacent to either the 5' LTR or the 3' LTR nucleic acid sequence, and a nucleic acid sequence encoding a transgene located between the 5' LTR and the 3' LTR. The replication-defective adenoviral vector is packaged in the adenoviral capsid proteins, to produce infective adenovirus.

An adenoviral vector is provided, including: (1) a 5' retroviral LTR nucleic acid sequence, wherein the 5' retroviral LTR nucleic acid sequence includes a U3, R, U5 nucleic acid sequence and a portion of a nucleic acid sequence encoding a retroviral envelope polypeptide; (2) a 3' retroviral LTR nucleic acid sequence, wherein the 3' retroviral LTR includes an U3, R, U5 nucleic acid sequence and a portion of a nucleic acid sequence encoding a retroviral envelope polypeptide; (3) a nucleic acid sequence encoding a transgene located between the 5' LTR and the 3' LTR; and (4) a retroviral packaging sequence. In one embodiment, the adenoviral vector is replication defective.

In another embodiment, an adenoviral vector is provided that includes an adenoviral polynucleotide sequence comprising a nucleic acid encoding a transgene, a 5' and a 3' retroviral LTR, a retroviral packaging signal, and a portion of a retroviral envelope polypeptide, wherein the adenoviral polynucleotide sequence does not encode one or more of E1, E3 or E4.

A method for transfecting a cell is also provided. The method includes contacting the cell with an adenovirus including an adenoviral vector with a 5' retroviral LTR and a 3' retroviral LTR flanking a transgene, wherein the adenoviral vector is functionally deleted for an essential gene, and wherein the cell is not able to produce viral particles. The contact results in transfection of the cell.

In another embodiment, method is provided for stably introducing a transgene into a cell that is not able to produce viral particles with a single viral vector. The cell is contacted with an adenovirus including an adenoviral vector with a 5' retroviral LTR and a 3' retroviral LTR flanking a transgene. In one embodiment, the adenoviral vector is functionally deleted for an essential gene. The adenoviral vector is thus introduced into the cell, and no other viral vector is introduced into the cell.

A method is also provided for preventing or treating a disorder in a subject, such as a genetic disorder, for example a disorder caused by a failure to adequately express a gene product. The method includes introducing into a cell of the subject a therapeutically effective amount of an adenoviral vector of the invention, wherein the cell is unable to produce viral particles. The introduction of the hybrid adenoviral vector results in the stable genetic transfection of the cell and expression of the transgene, such that a symptom of the disorder is alleviated or the disorder is prevented.

In yet another embodiment, a method for treating a subject is provided that includes contacting a cell of the subject with a therapeutically effective amount of a replication defective adenovirus. The adenovirus includes a replication-defective adenoviral vector with a 5' retroviral LTR and a 3 retroviral LTR flanking a transgene, wherein the adenoviral vector is functionally deleted for an essential gene. The contact results in the adenoviral vector integrating into a chromosome of the cell and expressing the transgene in the cell. The cell of the subject is not contacted with any other virus, and the expression of the transgene treats the subject.

In a further embodiment, a pharmaceutical composition is provided that includes: (1) an adenoviral vector that includes a nucleic acid sequence encoding a 5' retroviral LTR, a 3' retroviral LTR, a portion of a retroviral envelope protein, and a transgene located between the 5' LTR and the 3' LTR, wherein the nucleic acid encoding the 5' retroviral LTR, the 3' retroviral LTR, the portion of the retroviral envelope polypeptide, the transgene, and the viral packaging sequence are inserted into a replication-defective adenoviral vector nucleic acid; and (2) a pharmaceutically acceptable carrier.

BRIEF DESCRIPTION OF THE DRAWINGS

FIG. 1A is bar graph showing expression in dividing cells. Open bars are cells infected with AdCMV-luc, and filled bars are cells infected with AdCMV-luc. FIG. 1B is bar graph showing expression in non-dividing cells. Open bars are cells infected with AdCMV-luc, and filled bars are cells infected with AdCMV-luc. FIG. 1C is a graph of the luciferase activity in rat submandibular gland after retrograde ductal infusion of virus ($1 \times 10^9$ pfu/gland). FIG. 1D is a graph of the levels of luciferase in the overlying cortex. FIG. 1E is a graph of the levels of luciferase and in the caudate nucleus following direct injection of $1 \times 10^8$ pfu of virus into the caudate nucleus. Animals received either AdCMV-luc (dashed line) or AdLTR-luc (solid line). The data are the mean±SD of three assays for cells in vitro and three samples from three rats in vivo.

FIG. 10 is a tabulation of the number and location of the restriction sites in the MoMLV 5' LTR FIG. 11 is a tabulation of the number and location of the restriction sites in the MoMLV 3' LTR.

FIG. 12 B is a partial diagram of SalI and XhoI enzyme target sites in AdLTR-luc. FIG. 12 E A is a partial diagram of Xba I/Kpn I, Bam HI/Sac I or Bam HI/Nco enzyme target sites in AdLTR-luc.

DETAILED DESCRIPTION OF SEVERAL SPECIFIC EMBODIMENTS

Definitions

Figure 1:
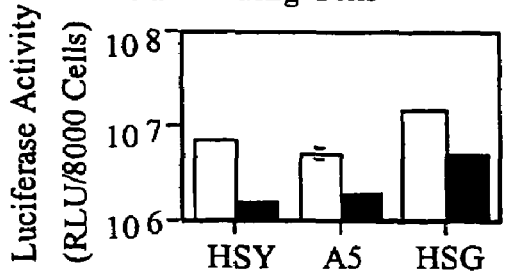
FIGS. 1A-E is a series of graphs showing luciferase expression by AdLTR-luc in quiescent and dividing cells, brain and submandibular gland. The following cells were used in vitro: the salivary epithelial cell lines HSY (human), A5 (rat), HSG (human), mononuclear cells (Mo) and macrophages (Ma) from normal human peripheral blood, hippocampus neurons from rat brain (Hi).
Figure 1:
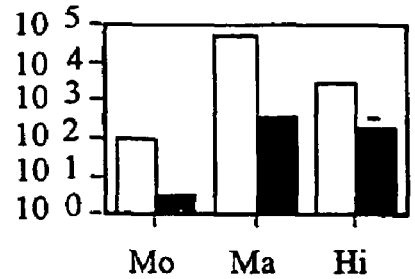
Figure 1:
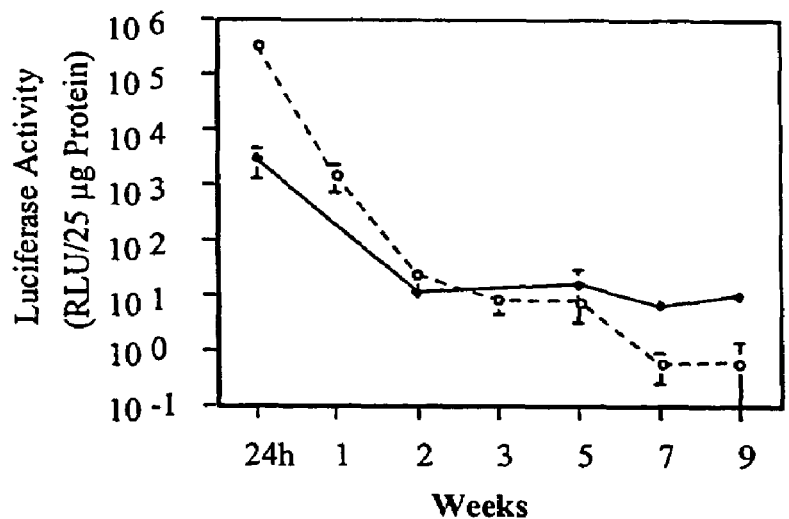
Figure 1:
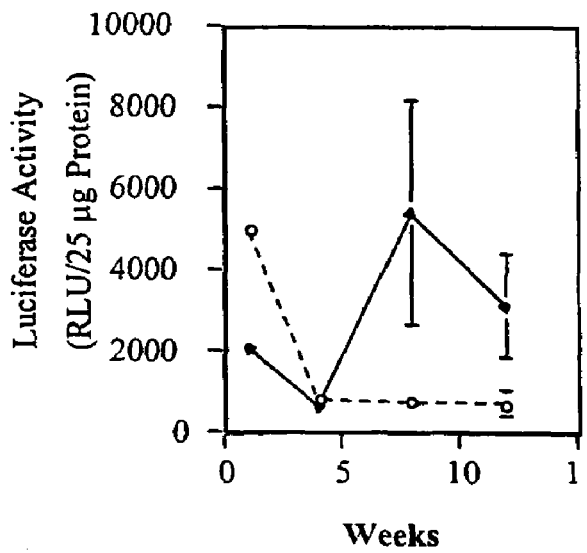
Figure 1:
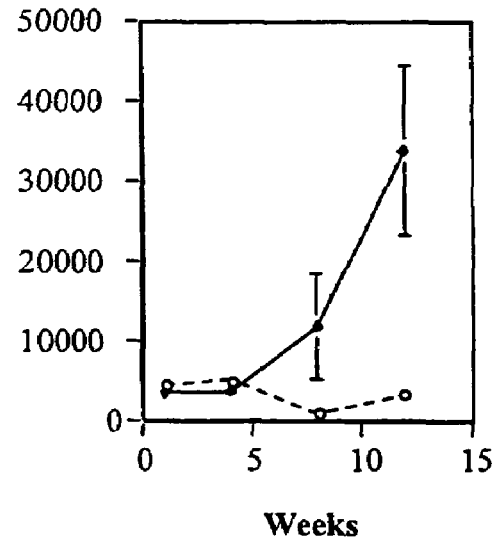

The following definitions and methods are provided to better define the present invention, and to guide those of ordinary skill in the art in the practice of the present invention. It must be noted that as used herein and in the appended claims, the singular forms "a", "an", and "the" include plural referents unless the context clearly dictates otherwise. Thus, for example, reference to "a cell" includes a plurality of such cells and reference to "the vector" includes reference to one or more vectors and equivalents thereof known to those skilled in the art, and so forth.

Unless defined otherwise, all technical and scientific terms used herein have the same meaning as commonly understood to one of ordinary skill in the art to which this invention belongs.

Adenovirus: An family of icosahedral (20-sided) viruses that contain DNA. Two genuses, Mastadenovirus and Aviadenovirus are included in the adenovirus family. While there are over 40 serotype strains of adenovirus, most of which cause benign respiratory tract infections in humans, subgroup C serotypes 2 or 5 are predominantly used as vectors. The life cycle does not normally involve integration into the host genome, rather an adenovirus replicates as episomal elements in the nucleus of the host cell and does not insert into the genome. A "adenoviral vector" is a vector derived from publicly available adenoviral DNA. At a minimum, an adenoviral vector includes the inverted terminal repetitions of an adenovirus. Vectors can include elements from other viruses, such as retroviruses.

Animal: Living multicellular vertebrate organisms, a category which includes, for example, mammals and birds.

Antisense, Sense, and Antigene: Double-stranded DNA (dsDNA) has two strands, a 5'->3' strand, referred to as the plus strand, and a 3'->5' strand, referred to as the minus strand. Because RNA polymerase adds nucleic acids in a 5'->3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional or physical binding assays. Binding may be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Southern blotting, Northern blotting, dot blotting and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Capsid: The protein covering, or outer coat, of a virus particle. The capsid is a protein coat that covers the nucleoprotein core or nucleic acid of a virion. The capsid generally shows icosahedral symmetry and in some viruses (not adenoviruses) is enclosed in an envelope. The capsid is built up of subunits (some integer multiple of 60, the number required to give strict icosahedral symmetry) that self assemble in a pattern typical of a particular virus. The subunits are often packed, in smaller capsids, into 5 or 6 membered rings (pentamers or hexamers) that constitute the morphological unit (capsomere). A capsid is required for viral infection of a cell.

Envelope polypeptide or Env: An "env" polypeptide is a retroviral "envelope" protein which encodes the surface (SU) glycoprotein and the transmembrane (TM) protein of the virion. The SU glycoprotein and the TM protein form a complex that interacts specifically with cellular receptors. In one embodiment, a "portion" of a env protein refers to at least 15 consecutive amino acids of a env protein sequence. In one embodiment, a "portion" of an env protein refers to at least 25 consecutive amino acids of an env protein sequence. In yet another embodiment, a "portion" of an env protein refers to at least 35 consecutive amino acids of an env protein sequence.

Essential Gene: A gene required for viral replication, packaging or infection. Deletion of an essential gene renders a virus replication defective. For example, in an adenovirus, E1 and E2 are essential genes.

Functional Deletion: A mutation in a sequence that has an effect equivalent to deletion of the sequence, for example eliminating the function of a packaging signal or an essential gene product by a deletion, insertion, or substitution.

Functionally Equivalent: Sequence alterations, in either the transfer or packaging vector sequences, that yield the same results as described herein. Such sequence alterations can include, but are not limited to, conservative substitutions, deletions, mutations, frameshifts, and insertions. In an adenoviral vector deleted for E1 of the invention, deletions in an another gene, such as E4, are functionally equivalent to a similar vector including an E3 deletion. In addition, alterations of the adenoviral vector sequence which yield enhanced encapsidation of the transfer vector genome, are functionally equivalent to the transfer vector of the invention.

Gene, Genome, and Genetic Target: The terms "gene," "genome," and "genetic target" include both DNA and RNA. Generally, a gene is a sequence of DNA or RNA that codes for a protein. A "target" sequence is a sequence to which an antisense or sense oligonucleotide or analog specifically hybridizes.

Group Specific Antigen Polypeptide or Gag: A "gag" protein is a retroviral "group specific antigen" polypeptide which is proteolytically processed into the mature proteins MA (matrix), CA (capsid), and NC (nucleocapsid), and other proteins that are numerically designated.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Figure 4:
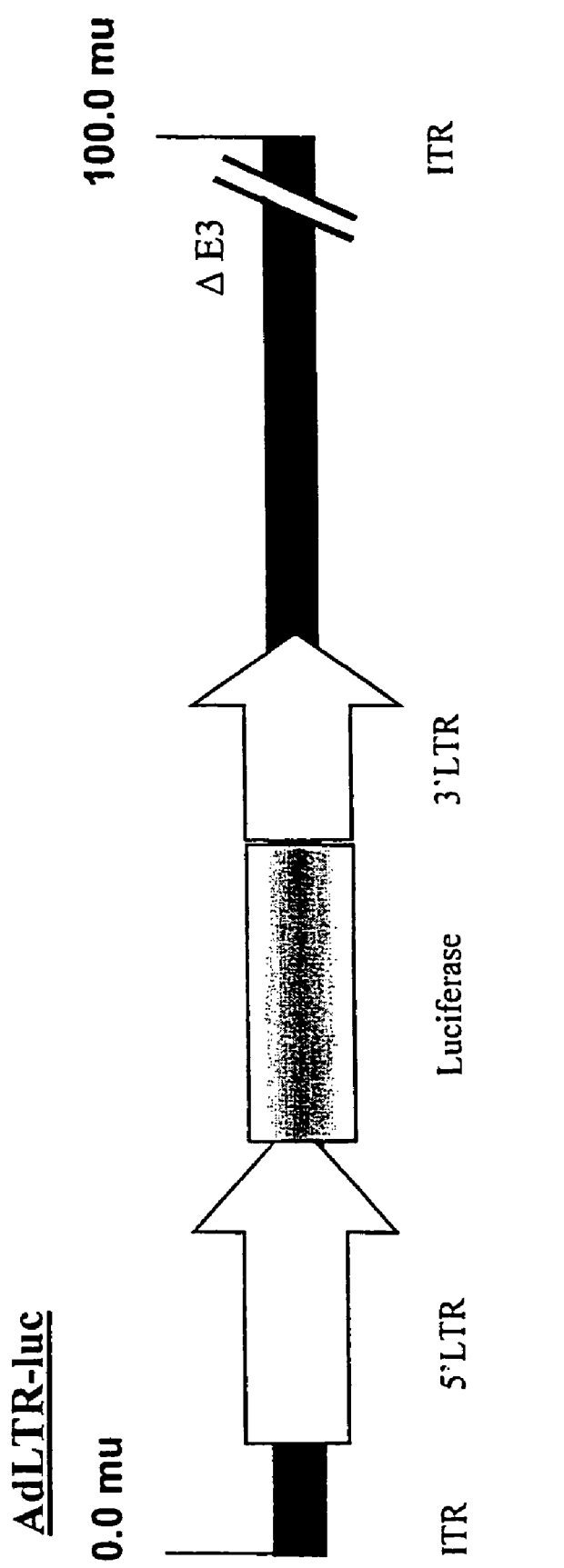
FIG. 4 is a schematic diagram of AdLTR-luc. AdLTR-luc contains 2.7 kb of the 5'LTR and 1 kb of the 3'LTR from MoMLV sequences, luciferase as a reporter gene, and the SV40 polyadenylation sequence downstream of the luciferase cDNA. The 5' LTR includes a portion of the MoMLV envelope gene, as does the 3' LTR. The 3' and 5' ITR of MoMLV are also included.
Figure 6:
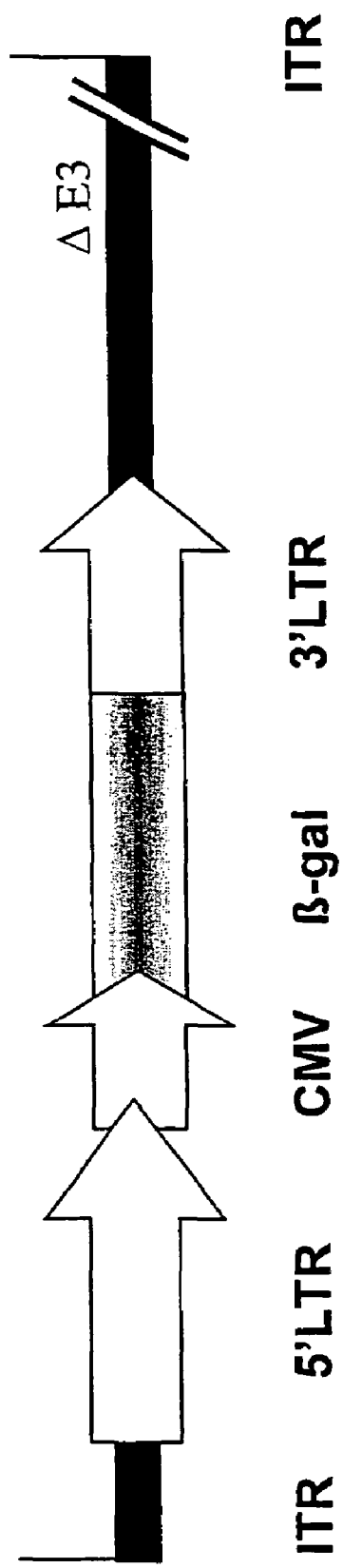
FIG. 6 is a schematic diagram of AdLTR-βgal.
Figure 7:
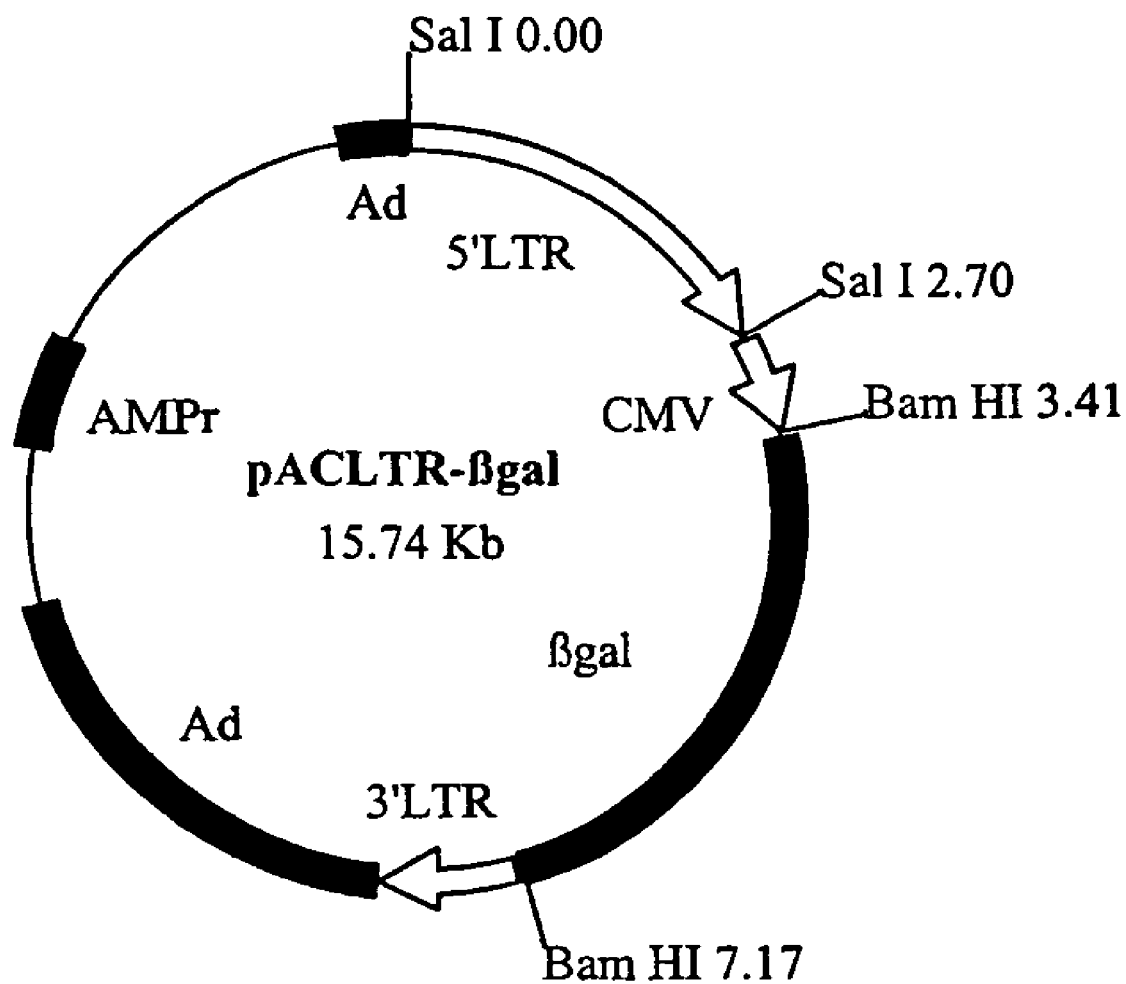
FIG. 7 is a schematic diagram of pACLTR-βgal.
Figure 8:
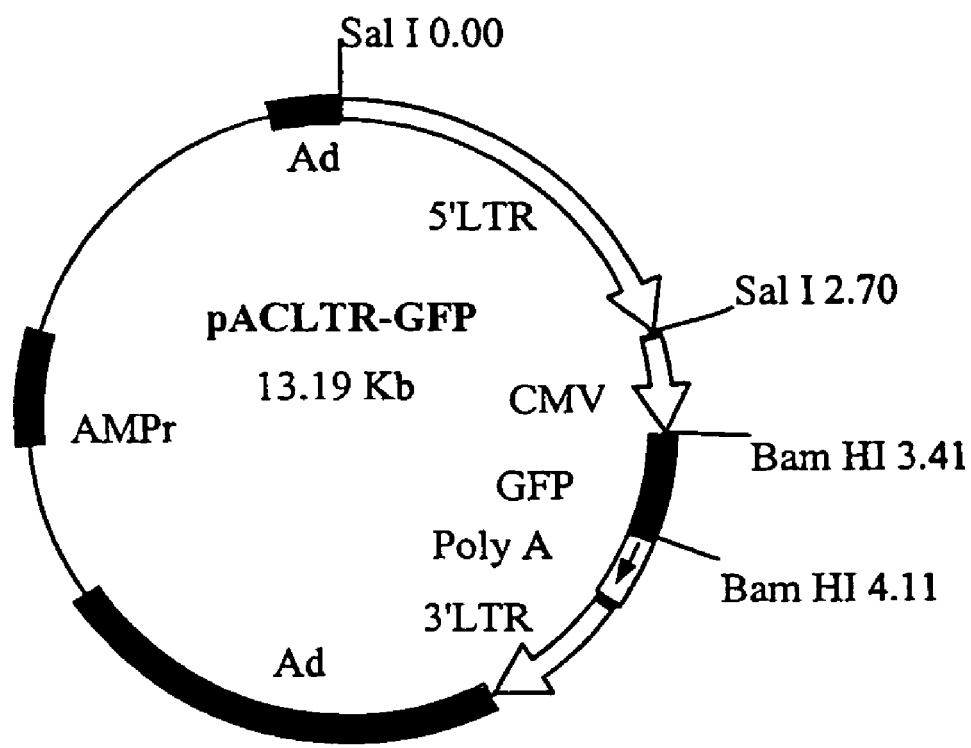
FIG. 8 is a schematic diagram of pACLTR-GFP.
Figure 9:
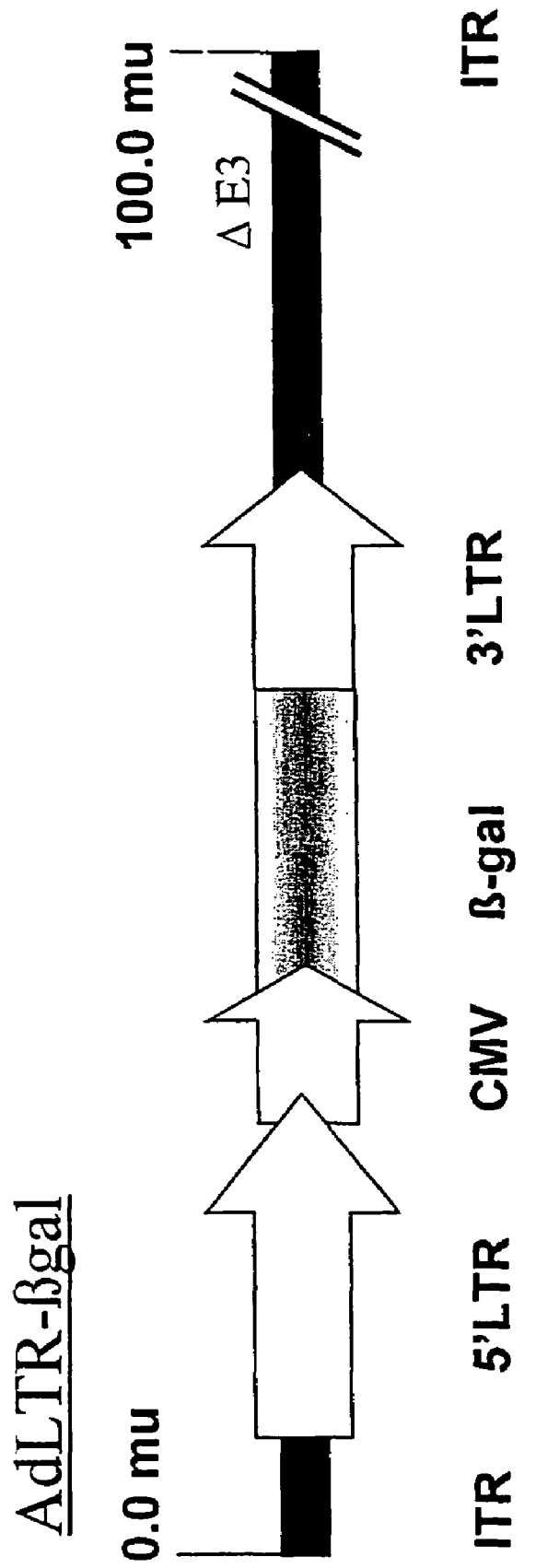
FIG. 9 is a schematic diagram of AdLTR-βgal.

Hybrid Adenoviral Vector: An adenoviral vector that includes a sequence from a retrovirus incorporated into the adenoviral vector. Specific non-limiting examples of hybrid adenoviral vectors are AdLTRluc (FIG. 4) and AdLTR-βgal (FIG. 6). In one embodiment, a 5' and a 3' LTR from a retrovirus, (e.g. MoMLV) are inserted in an adenovirus 5 vector. A hybrid adenoviral vector includes, at a minimum, the inverted terminal repeats of an adenovirus and at least one element of a retrovirus. In one specific non-limiting example the hybrid adenoviral vector includes the inverted terminal repeats and a 5' LTR and a 3' LTR of a retrovirus. The adenoviral 5 vector can also be modified. Thus in another embodiment the adenviral vector is modified to delete an adenoviral gene, (e.g. E1 and E3).

Infective: A virus or vector is "infective" when it transduces a cell, replicates, and (without the benefit of any complementary virus or vector) spreads progeny vectors or viruses of the same type as the original transducing virus or vector to other cells in an organism or cell culture, where the progeny vectors or viruses have the same ability to reproduce and spread throughout the organism or cell culture. Thus, for example, a nucleic acid encoding an adenoviral particle is not infective if the nucleic acid cannot be packaged (e.g. if the adenoviral particle lacks a packaging site), even though the nucleic acid can be used to transfect a cell. Similarly, an adenoviral nucleic acid packaged by an adenovrial particle is not infective if it does not encode the adenoviral capsid proteins that it is packaged in.

Integration: A virus "integrates" into cellular DNA when the nucleic acid of the virus is incorporated into the cellular genome (i.e. into a chromosome).

Inverted Terminal Repetition (ITR): A sequence found in adenovirus located the end of each strand, these sequences are inverted repeats. When the virus is denatured the repeats enable the formation of "panhandle" structures of 100-140 bp from the single nucleic acid strands.

Isolated: An "isolated" nucleic acid has been substantially separated or purified away from other nucleic acid sequences and in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Long Terminal Repeat or LTR: An "LTR" is a "long terminal repeat" that is generated as a DNA duplex at both ends of the retrovirus when a retrovirus integrates into a host genome. The 5' LTR includes a U3, R, and U5 nucleic acid element. The 3' LTR also includes U3, R, and U5 nucleic acid element. In a replication competent retrovirus, LTRs also contain an active RNA polymerase II promoter which allows transcription of the integrated provirus by host cell RNA polymerase II to generate new copies of the retroviral RNA genome.

An integrated retrovirus has two LTRs, one at the 5' end and one at the 3' end of the viral genome. The "5' LTR" is located at the 5' end of the retroviral DNA, and the "3'LTR" is located at the 3' end of the retroviral DNA.

Mammal: This term includes both human and non-human mammals. Similarly, the term "subject" includes both human and veterinary subjects.

Nucleic acid sequence (or polynucleotide): A deoxyribonucleotide or ribonucleotide polymer in either single or double stranded form, and unless otherwise limited, encompasses known analogues of natural nucleotides that hybridize to nucleic acids in a manner similar to naturally occurring nucleotides, and includes polynucleotides encoding full length proteins and/or fragments of such full length proteins which can function as a therapeutic agent. A polynucleotide is generally a linear nucleotide sequence, including sequences of greater than 100 nucleotide bases in length.

Nucleotide: "Nucleotide" includes, but is not limited to, a monomer that includes a base linked to a sugar, as in DNA and RNA, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Packaging cell: A cell that provides packaging functions in trans for a gene introduced into a cell with a transfer vector, but which does not encapsidate its own viral RNA.

Packaging Signal: A complex signal, also known as "φ", that is important for the packaging of virus in viral particles.

Packaging Vector: Packaging vector nucleic acids lack the nucleic acids necessary for packaging of a DNA corresponding to the packaging vector nucleic acid into an adenoviral capsid. That is, packaging vector nucleic acids are not themselves encapsidated in the viral particles which they encode, i.e. they are not infective. The packaging vector optionally includes all of the components necessary for production of viral particles, or optionally includes a subset of the components necessary for viral packaging. For instance, a packaging cell may be transformed with more than one packaging vector, each of which has a complementary role in the production of an adenoviral particle.

Two (or more) adenoviral-based packaging vectors are "complementary" when they together encode all of the functions necessary for adenovirus packaging, and when each individually does not encode all of the functions necessary for packaging. For example, when two vectors transduce a single cell and together they encode the information for production of adenovirus packaging particles, the two vectors are "complementary." The use of complementary vectors increases the safety of any packaging cell made by transformation with a packaging vector by reducing the possibility that a recombination event will produce an infective virus.

Adenoviral packaging cell lines are cells including nucleic acid molecules that encode adenoviral capsid proteins which can be used to form adenoviral particles. The adenoviral particles are competent to package target adenovirus which has a packaging site.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Additional definitions of common terms in molecular biology may be found in Lewin, B. "Genes V" published by Oxford University Press.

Polymerase or Pol: A "pol" protein is a retroviral reverse transcriptase, which contains both DNA polymerase and associated RNAse H activities, and Integrase (IN). Pol mediates replication of the viral genome in vivo. The ends of the newly synthesized linear double-stranded viral DNA are recognized and two nucleotides from the 3' end of each strand are removed. These DNA ends are joined to a target DNA at random sites.

Polypeptide: Any chain of amino acids, regardless of length or post-translational modification (e.g., glycosylation or phosphorylation). In one embodiment, a polypeptide can be a "marker" polypeptide, which is used to identify cells that express the polypeptide. A marker polypeptide can be detected using methods known to one of skill in the art, including enzymatic assays and assays utilizing antibodies (e.g. ELISA or immunohistochemistry). Specific non-limiting examples of a maker protein are luciferase, green fluorescent protein (GFP), or beta-galactosidase. In another embodiment, a polypeptide is a "therapeutic" polypeptide, which can be used to alleviate or relieve a symptom of a disorder. Specific, non-limiting examples of therapeutic polypeptides are cytokines or immunomodulators, hormones, neurotransmitters, or enzymes.

Probes and primers: A probe comprises an isolated nucleic acid attached to a detectable label or reporter molecule. Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive contiguous nucleotides from a DNA sequence will anneal to a target with a higher specificity than a corresponding primer of only 15 contiguous nucleotides. Thus, in order to obtain greater specificity, probes and primers may be selected that comprise 20, 25, 30, 35, 40, 50 or more contiguous nucleotides.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements.

Purified: The term purified does not require absolute purity; rather, it is intended as a relative term. Thus, for example, a purified protein preparation is one in which the protein is more pure than the protein in its natural environment within a cell. For example, a preparation of a protein is purified such that the protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Replication defective: A virus is replication defective if it cannot replicate in a host cell.

Retrovirus: Any virus in the family Retroviridae. These viruses have similar characteristics, specifically they share a replicative strategy. This strategy includes as essential steps reverse transcription of the virion RNA into linear double-stranded DNA, and the subsequent integration of this DNA into the genome of the cell. All native retroviruses contain three major coding domains with information for virion proteins: gag, pol and env. In one embodiment, a retrovirus is an avian sarcoma and leukosis virus, a mammalian B-type virus, a Murine leukemia-related virus, a Human T-cell leukemia-bovine leukemia virus, a D-type virus, a lentivirus, or a spumavirus. In another embodiment, the virus is a Rous sarcoma virus, a mouse mammary tumor virus, a human T-cell leukemia virus, a Mason-Pzifer monkey virus, a human immunodeficiency virus, a human foamy virus, or a Molony Leukemia Virus. A retrovirus generally contains three genes known as "gag," "pol," and "env."

RNA: All types of RNA, including viral genomic RNA and mRNA.

Sequence identity: The similarity between two nucleic acid sequences, such as an antisense sequence and a gene, or two amino acid sequences, is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, *Methods in Molec. Biology* 24:307-331, 1988; Higgins and Sharp, *Gene* 73:237-244, 1988; Higgins and Sharp, *CABIOS* 5:151-153, 1989; Corpet et al., *Nucleic Acids Research* 16:10881-90, 1988; Huang et al., *Computer Applications in BioSciences* 8:155-65, 1992; and Pearson et al., *Methods in Molecular Biology* 24:307-31, 1994

The NCBI Basic Local Alignment Search Tool (BLAST) (Altschul et al., *J. Mol. Biol.* 215:403-410, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at the NCBI website (BLAST)A description of how to determine sequence identity using this program is available at the NCBI website (BLAST).

Homologs of a protein, such as a marker or a therapeutic protein, is typically characterized by possession of at least 70% sequence identity counted over the full length alignment with the disclosed amino acid sequence using the NCBI Blast 2.0, gapped blastp set to default parameters. Such homologous peptides will more preferably possess at least 75%, more preferably at least 80% and still more preferably at least 90% or 95% sequence identity determined by this method. When less than the entire sequence is being compared for sequence identity, homologs will possess at least 75%, 85%, 90% or 95% sequence identity over short windows of 10-20 amino acids. Methods for determining sequence identity over such short windows are described at the NCBI website (BLAST). One of skill in the art will appreciate that these sequence identity ranges are provided for guidance only; it is entirely possible that strongly significant homologs or other variants could be obtained that fall outside of the ranges provided.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website (BLAST).

One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The Tm is the temperature (under defined ionic strength and pH) at which 50% of the target sequence remains hybridized to a perfectly matched probe or complementary strand. Conditions for nucleic acid hybridization and calculation of stringencies can be found in Sambrook et al. (*Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, N.Y., 1993). Nucleic acid molecules that hybridize under stringent conditions to an encoding sequence will typically hybridize to a probe based on either an entire encoding sequence or selected portions of the encoding sequence under wash conditions of 2×SSC at 50° C.

Supernatant: The culture medium in which a cell is grown. The culture medium includes material from the cell. If the cell is infected with a virus, the supernatant can include viral particles.

Target sequence: "Target sequence" is a portion of ssDNA, dsDNA or RNA that, upon hybridization to a therapeutically effective antisense oligonucleotide or oligonucleotide analog, results in the inhibition of expression of the target sequence. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount: An amount of a therapeutic protein or antisense molecule effective to inhibit or treat a disease. Although this amount varies depending on the severity and nature of a condition being treated, examples of effective amounts are tissue concentrations that are effective to provide relief of a symptom.

Therapeutically Effective Oligonucleotides: Characterized by their ability to inhibit the expression of a gene of interest. Complete inhibition is not necessary for therapeutic effectiveness. Therapeutically effective oligonucleotides are characterized by their ability to inhibit the expression of the gene of interest. Inhibition is defined as any reduction in expression seen when compared to production in the absence of the oligonucleotide or oligonucleotide analog. Additionally, some oligonucleotides will be capable of inhibiting the expression of a gene of interest by at least 15%, 30%, 40%, 50%, 60%, or 70%, or more.

Therapeutically effective oligonucleotides are additionally characterized by being sufficiently complementary to nucleic acid sequences encoding a gene of interest. As described herein, sufficient complementary means that the therapeutically effective oligonucleotide can specifically disrupt the expression of a gene, and not significantly alter the expression of other genes.

Transduced, Transfected, and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication. As used herein, the term transformation or "transduction" encompasses all techniques by which a nucleic acid molecule might be introduced into such a cell, including transfection with viral vectors, transformation with plasmid vectors, and introduction of naked DNA by electroporation, lipofection, and particle gun acceleration.

Transfer (or Shuttle) vector: A vector which shuttles a gene, but does not include all of the components necessary for production of adenoviral particles.

Transgene: An exogenous gene or nucleic acid sequence supplied by a vector. In one embodiment the transgene encodes a marker protein which can be detected using methods known to one of skill in the art. Specific non-limiting examples of a marker protein are luciferase, green fluorescent protein (GFP), or beta-galactosidase. In another embodiment, the transgene encodes a therapeutic protein, which can be used to alleviate or relieve a symptom of a disorder. Specific, non-limiting examples of therapeutic proteins are cytokines or immunomodulators, hormones, neurotransmitters, or enzymes. In another embodiment, the transgene encodes a therapeutically effective oligonucleotide (e.g. an antisense oligonucleotide), wherein expression of the oligonucleotide inhibits the expression of a target nucleic acid sequence. In a further embodiment, the transgene encodes an antisense nucleic acid or a ribozyme. In yet another embodiment, the transgene encodes an enzyme. Specific, non-limiting examples of enzymes are kinases, phosphorylases, deaminases, or any enzyme that converts pro-drugs to an active form of the drug.

The transgene can have the native regulatory sequences operably linked to the transgene (e.g. the wild-type promoter, found operably linked to the gene in a wild-type cell). Alternatively, a heterologous promoter can be operably linked to the transgene. In yet another embodiment, the viral LTR can be used to express the transgene.

Variant oligonucleotides and variant analogs: A variation of an oligonucleotide or an oligonucleotide analog is an oligomer having one or more base substitutions, one or more base deletions, and/or one or more base insertions, so long as the oligomer substantially retains the activity of the original oligonucleotide or analog, or has sufficient complementarity to a target sequence.

A variant oligonucleotide or analog may also hybridize with the target DNA or RNA, under stringency conditions as described above. A variant oligonucleotide or analog also exhibits sufficient complementarity with the target DNA or RNA of the original oligonucleotide or analog as described above.

Vector: A nucleic acid molecule as introduced into a host cell, thereby producing a transformed host cell. A vector may include nucleic acid sequences that permit it to replicate in the host cell, such as an origin of replication. A vector may also include sequences encoding one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. A vector may be a viral vector, derived from a virus, such as an adenoviral vector.

Viral Vectors and Viruses

Hybrid adenoviral vectors that provide highly efficient gene transfer to both dividing and non-dividing host cells have been developed. The hybrid adenoviral vectors integrate into the cellular genome such that a transgene is integrated into the cellular genome and is stably expressed. The hybrid adenoviral vectors are replication-defective, as they are deficient in the production of an essential gene product. One specific, non-limiting example of an essential adenoviral gene is E1. In other specific, non-limiting examples, the adenoviral vector is deficient for the production of E1, E3, and E4, or E1, E2, E3, and E4.

Other strategies have required the use of multiple adenoviral vectors to provide transcomplementing functions to support the production of a recombinant vector. The present system is unique in that all the required functions are present in the hybrid adenoviral vector itself. In addition, no viral particles are produced once the hybrid adenoviral vector enters the host cell.

The adenoviral vector includes a 5' retroviral LTR nucleic acid sequence and a 3' retroviral LTR nucleic acid sequence. In one embodiment, a nucleic acid sequence encoding a portion of a retroviral envelope polypeptide adjacent to either the 5' LTR or the 3' LTR nucleic acid sequence. The 5' retroviral LTR, the 3' retroviral LTR, and the envelope polypeptide can be from any known retrovirus. In one specific, non-limiting example, a 5 retroviral LTR, a 3' retroviral LTR, an envelope sequence from MoMLV is utilized. A packaging sequence from the retrovirus (e.g. MoMLV) can also be included.

A 5' retroviral LTR is included in the hybrid adenoviral vector. In one embodiment, an about 2.7 kb sequence of MoMLV including the 5' LTR is utilized in the hybrid adenoviral vector (see Example 1 and FIG. 10). This sequence includes the 5' LTR, the packaging signal, and a portion of the MoMLV envelope polypeptide. Thus, a packaging signal can be included in a hybrid adenoviral vector of the invention. In another embodiment, about 1.0 kb of MoMLV including the 5'LTR is utilized in a hybrid adenoviral vector. This sequence includes the 5' LTR and a portion of the viral envelope protein, but does not include the packaging signal. In one specific, non-limiting example the 1.0 kb of MoMLV is from about base pair 1155 to about base pair 2168 (a fragment 1,013 base pairs in length). In yet another embodiment, about 0.5 kb of MoMLV including the 5' LTR is utilized in the hybrid adenoviral vector. In a further embodiment, a retroviral packaging sequence is located downstream of this 5'LTR.

A 3' retroviral LTR is also included in the hybrid adenoviral vector. In one embodiment, about 1.0 kb of MoMLV including the 3' LTR is utilized in the hybrid adenoviral vector (see Example 1 and FIG. 11). This sequence includes the 3' LTR and a portion of the viral envelope protein. In a further embodiment, about 0.5 kb of MoMLV including a 3' LTR is utilized in the hybrid adenoviral vector.

The adenoviral vector also includes a nucleic acid sequence encoding a transgene (see below) located between the 5' LTR and the 3' LTR. Exemplary constructs and plasmids including these constructs are shown in FIGS. 4, 5, 6, 7, 8 and 9. These hybrid adenoviral vectors achieve stable expression of the transgene as they integrate into the cellular genome. Stable transgene expression is achieved in both dividing and non-dividing cells. The adenoviral vectors can be used to infect any cell of interest, either in vivo or in vitro.

The hybrid adenoviral vector can be packaged in adenoviral capsid proteins, thereby producing infective adenovirus. Any method known to one of skill in the art for producing adenoviral capsid proteins, and for packaging adenoviral vectors can be utilized with the hybrid adenoviral vectors of the invention. For example, one specific, non-limiting method of packaging hybrid adenoviral vectors is the use of 293 cells.

Transgenes

The transgene can be any sequence of interest. In one embodiment, the transgene is a nucleic acid sequence encoding a marker (e.g. luciferase (luc), β-galactosidase (β-gal), or green fluorescent protein (GFP)). In another embodiment, the transgene encodes a therapeutic polypeptide. A therapeutic polypeptide is any polypeptide which can be used to treat a disorder in a subject or cell. Specific, non-limiting examples of therapeutic polypeptides include cytokine and immunomodulators, hormones, and neurotransmitters. In a subject or cell deficient for a specific polypeptide, a therapeutic polypeptide can be that specific polypeptide, can be a variant of that specific polypeptide, or can be another polypeptide that serves the same function in the subject or cell. Specific non-limiting examples of therapeutic polypeptides of use with the invention include, but are not limited to, IL-10, IL-6, erythropoietin (EPO), growth hormone (GH), alpha anti-trypsin), and alpha-galactosidase A.

In one embodiment of the present invention, the hybrid retrovirus can include a transgene that encodes an antisense molecule, which includes antigene molecules. Antisense and sense molecules include oligonucleotides that interfere with expression of DNA or RNA. In one aspect of the present invention, the antisense or sense molecules can bind to the target RNA, or otherwise interfere with the translation of the target RNA. In another aspect of the invention, the antisense molecule induces Rnase H-mediated RNA degradation, or inhibits RNA polymerase II. In another aspect of the invention, the antisense molecule binds to the target DNA and disrupts transcription.

For instance, antisense or antigene molecules can have complementary nucleotide sequences to the target DNA or RNA. These complementary nucleotide sequences can specifically hybridize to the target DNA or RNA by Watson-Crick base pair formation or Hoogsteen base pair formation.

Expression of the transgene in transfected cells can be evaluated by a variety of techniques including ELISA, Northern blot and other standard protein assays which allow one to determine that the transgene is being expressed (for example assaying for the conversion of L-dopa to L-dopamine after transfecting cells with the AADC gene). Transfected cells can be analyzed for cellular RNA by extraction of the RNA by standard methods, and by measurement of absorbance of light at set wavelengths. Northern blot and slot-blot hybridization can be used to quantify RNA.

Without further elaboration, it is believed that one skilled in the art can, using this description, utilize the present invention to its fullest extent. The following examples are illustrative only, and not limiting of the remainder of the disclosure in any way whatsoever.

Example 1

Construction of Recombinant Viral Vectors

The replication-deficient recombinant adenoviral vectors used are based on the adenovirus type 5 (Ad5) genome (see Becker et al., 1994, "Use of Recombinant Adenovirus for Metabolic Engineering of Mammalian Cells," in: *Method in Cell Biology* 43:161-189, herein incorporated by reference). E1 deletion was achieved by recombination of the pAC shuttle plasmid with pJM17. 2.7 kb or pBHG10 (Microbix Biosystems; Ontario, Calif.) of 5'LTR (which includes part of the envelope gene [1.5 kb], the 5'LTR [0.57 kb], and the packaging sequence [0.63 kb]) and 1 kb of 3'LTR (which contains a small part (~0.5 kb) of the envelope gene and an intact 3' LTR). A restriction map of the 5' LTR is shown in FIG. 10. A restriction map of the 3' LTR is shown in FIG. 11.

Figure 5:
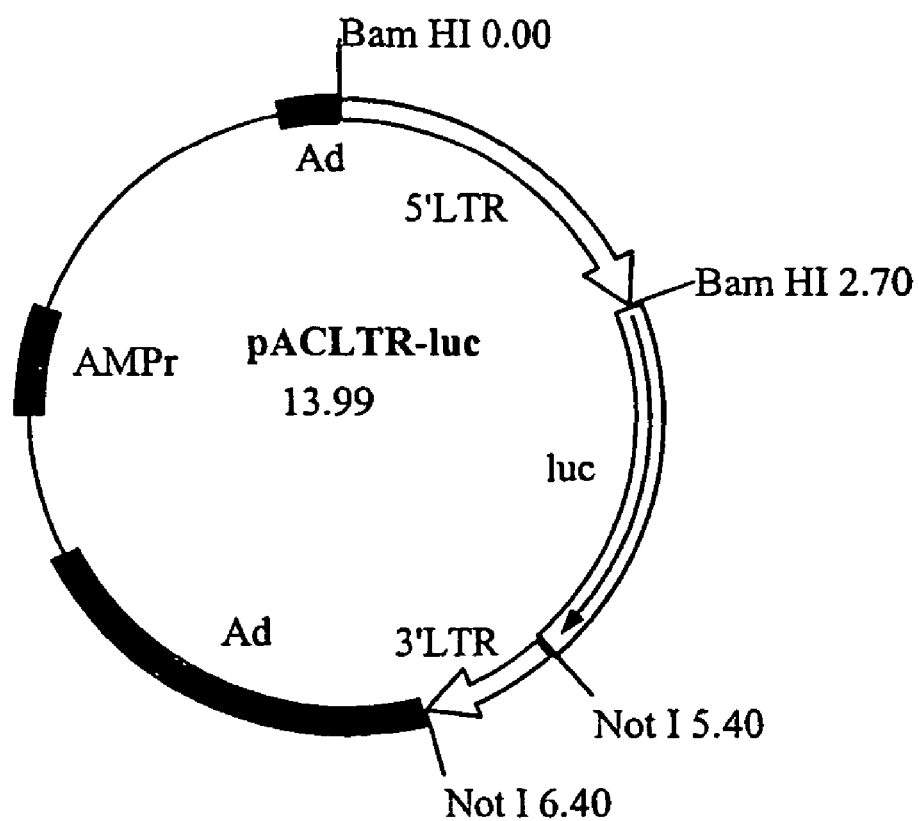
FIG. 5 is a schematic diagram of the plasmid pACLTR-luc.

MoMLV sequences were cleaved by EcoR I from the plasmid pXT1 (Stratagene, Catalog number 214201, La Jolla, Calif.) (Boulter and Wagner, *Nucleic Acids Res.* 15: 7194, 1987). Not I linkers were added to both ends of the 5'LTR fragment and BamH I linkers were added to both of ends of the 3'LTR fragment. Then, these two fragments were ligated into pAC (LTR sequences were placed in the deleted E1 adenoviral region), an adenoviral shuttle vector (from Dr. C. Newgard). Thus, this construct did not contain any gag or pol sequences from MoMLV. The luciferase (luc) fragment was cleaved from the plasmid pGL2-Basic (base pairs 76-1725 of the pGL2-Basic Vector, Promega, Madison, Wis.) and ligated between the 5'LTR and 3'LTR sequences. The luciferase gene was driven by the 5'LTR promoter. This plasmid was pACLTR-luc (FIG. 5). The recombinant adenovirus, AdLTR-luc (FIG. 4), was generated by homologous recombination of pACLTR-luc with the pBHG10 plasmid in 293 cells. AdCMV-luc was constructed as a non-integrating control adenoviral vector (Becker, et al., Use of recombinant adenovirus for metabolic engineering of mammalian cells, In *Methods in Cell Biology*. (ed. Roth, M. G.), Academic press, San Diego, pp. 161-189, 1994). The vector pACLTR-βgal (FIG. 7) was constructed using sequence encoding βgalactosidase that were isolated from the eukaryotic vector pSV—βgalactosidase (Promega Catalog #E1081). The recombinant adenovirus, AdLTR—βgal (FIG. 6), was also generated by homologous recombination. An additional construct including the nucleic acid encoding green fluorescent protein, pACTLR-GFP (FIG. 8) was also constructed.

Example 2

Experimental Methods

Cell culture: The human mononuclear cells and macrophages were obtained from the peripheral blood of normal volunteers. The cells were separated on Ficoll Hypaque, and washed twice with PBS. The mononuclear cells were cultured in suspension in RPMI 1640 with 10% human serum for 2 weeks before infection. The macrophages were adherent to the bottom of the flask after the mononuclear cells from peripheral blood were cultured for a week. The supernatant was replaced by fresh growth medium twice a week for 25 days before infection.

Hippocampus neurons (Dr. Z. G. Jiang, MH, NIH, Bethesda, Md.), were obtained from Tac:N(SD)fBR rats at 18 gestational days. Hippocampus tissue was cut into 1 mm cubes and then triturated by using fire-restricted Pasteur pipettes to achieve single cells. The cells were seeded at a density of 40,000/well in a 96-well plate, and cultured in neurobasal medium supplemented with 1×B27 and 2 mM glutamine for two weeks before infection. This method yields cultures containing 95-98% hippocampal neurons.

The HSY ductal cell line (Yanagawa, *Virchows Arch.* [B] 51, 1871-1885, 1986) was obtained from a human parotid adenocarcinoma and was grown in a mixture of 50% Dulbecco's MEM and 50% Ham's F 12 media. The ductal epithelial A5 cell line (Brown et al., *J. Oral Pathol. Med.* 18: 206-213, 1989) was derived from rat submandibular gland and grown in McCoy's 5A medium. The HSG cell line (Shirasuna et al., *Cancer* 48: 745-752, 1981) was obtained from an irradiated human submandibular gland, and was grown in DMEM/F12 medium.

All cells were infected with AdLTR-luc (FIG. 4) or AdCMV-luc at 50 pfu/cell.

Animal experiments: All experimental protocols were approved by the NIDR Animal Care and Use Committee (ACUC), and the NIH Biosafety Committee, and procedures were conducted in accordance with the IASP standards for the treatment of animals. Male Wistar rats (250-350 g, 3 months old) were used for in vivo studies. Rats were anesthetized with ketamine (36 μg/g body weight) and xylazine (3.2 μg/g body weight) intraperitoneally, and positioned in a stereotactic head frame. After access was achieved, they were infused over 15 minutes with 2 μl of virus ($1\times10^8$ pfu/rat) into the caudate nucleus [anteroposterior (AP), +2; mediolateral (ML), +3; dorsoventral (DV), −6.5]. At the $1^{st}$, $4^{th}$, $8^{th}$, and $12^{th}$ week, the tissues of the caudate nucleus and part of the cerebral cortex overlying the caudate nucleus and encompassing the needle track were collected for the luciferase or PCR assays. For the rat submandibular gland infection, the viruses ($1\times10^9$ pfu/gland) were injected by retrograde ductal instillation (Adesanya et al., *Human Gene Therapy* 7: 1085-1093, 1996). The other tissues were infected by a femoral vein injection of $1\times10^9$ pfu/rat.

Luciferase assay: Cells and tissues were homogenized when necessary, then lysed in cell lysis buffer (Promega) for 15 minutes. Fifty microliters of the cell lysate were added to 100 μl of luciferase substrate, and light output was measured with a luminometer. Results were expressed as relative light unit (RLU) per cell number or per μg protein.

PCR assays: The genomic DNA used in the PCR assays was extracted with either a Wizard Genomic DNA Purification Kit (Promega) or a Non-Organic DNA Extraction kit (Intergen, Purchase, N.Y.). Two hundred to 1000 ng of template DNA were used in each PCR reaction. The assay was capable of detecting 10 viral particles for each of the three targets described. The same amount of template DNA was added in all four PCR assays.

The primers 5'LTRS2 (5'-TCTCCACCACCATACT-GAACC-3', SEQ ID NO:1) and 5'LTRA1 (5'-TCAAAACTA-GAGCCTGGACC-3', SEQ ID NO:2) produced PCR 1. PCR 2 was amplified by 5'LTRS4 (5'-TGTGGTTCTGGTAG-GAGACG-3', SEQ ID NO:3) and 5'LTRA3 (5'-CCAACGTCTCTTCTTGACAT-3', SEQ ID NO:4). PCR 3 is a luciferase product and amplified by lucS2 (5'-AGGCGAAT-TATGTGTCAGAGG-3', SEQ ID NO:5) and lucA2 (5'-TTGGGGTGTTGTAACAATA-3', SEQ ID NO:6). If the results showed the PCR1 band was missing, the assays were repeated by increasing the amount of template DNA and re-amplifying at least twice.

Southern hybridization: The genomic DNA used in the Southern hybridization was extracted with a Non-Organic DNA Extraction kit (Intergen). Twenty micrograms of genomic DNA from each sample were digested with restriction enzymes and separated on a 1% agarose gel. Nucleic acids were then transferred to nylon membranes. The blots were hybridized with a $^{32}$P-radiolabelled luciferase probe (a 615 bp Hind III/EcoR I fragment from the 5'end of the luciferase cDNA) and autoradiographed.

FISH detection: The HSY cells infected with AdLTR-luc were cultured for a week after infection at 10 pfu/cell. The A5 cells infected with AdLTR-luc were cultured for two weeks. Rat spleen was infected with AdLTR-luc at $1\times10^9$ pfu/rat by intravenous injection. Spleen tissue was collected ten days after infection. FISH assays were carried out by SeeDNA Biotech INC. (Toronto, Canada). The data reported herein represent experiments with six separate cell preparations. Probe one was pACLTR-luc, which had 5' and 3'LTR and luciferase sequences. This probe was biotinylated with dATP using the BRL BioNick labeling kit. In the two probe hybridization, the second probe (E4 probe) was obtained from pJM17 between Hind III sites 30,697 and 36,143. The E4 probe was digoxigenin labeled with DATP, also using the BRL BioNick labeling kit. As a further control for the labeling conditions, the labels were switched for probe 1 and the E4 probe (i.e. pACLTR-luc was labeled with digoxigenin and the E4 probe with biotin). The procedure for FISH detection was performed according to published methods (Muller and Varmus, *EMBO J.* 66: 5092-5095, 1992).

Sequence of integration sites: The gene walking experiments were carried using a 5'RACE system (GibcoBRL, Rockville, Md.). Two specific antisense primers were used to sequence the junction; 5'LTR A3 (5'-CCAACGTCTCTTCT-TGACAT-3', SEQ ID NO:7) and 5'LTR A2 (5'-GAAACA-CAGTCAGACAGAGA-3', SEQ ID NO:8). The primer 5'LTR A3 was used to synthesize a single antisense strand of DNA from the 5'LTR. This single stranded DNA was tailed with dCTP. Further PCR assays were carried out using 5'LTR A2 and the Abridged Anchor primer (Gibco BRL) and Abridged Universal Amplification primer (Gibco BRL). The PCR products were cloned into the pCR 2.1 plasmid (Invitrogen, Carlsbad, Calif.), and the positive clones were sequenced.

Example 3

Gene Expression In Vitro and In Vivo

The salivary epithelial cells, HSY, A5 and HSG, grow readily in vitro. Human mononuclear cells and macrophages, and rat hippocampus neurons were cultured without cell proliferation. All of these cell types were readily infected by AdCMV-luc and AdLTR-luc (FIG. 1A, 1B).

In order to assess the time course of AdLTR-luc and AdCMV-luc persistence in vivo, rat submandibular glands were infected locally by retrograde ductal instillation of $1\times10^9$ pfu/gland. In submandibular glands the levels of luciferase activity dropped quickly in both virus groups during the two weeks following infection (FIG. 1C). The levels of luciferase activity were then maintained in the AdLTR-luc infected animals until 9 weeks (the last time point studied) while they continued to decline in the AdCMV-luc group. At the 9 week time point average luciferase activity in glands administered AdLTR-luc was 15-fold greater than in glands administrated AdCMV-luc (9.1 RLU/25 μg protein vs 0.6 RLU, respectively); this despite the CMV promoter being a much stronger promoter than the LTR (Hodgson, The retroelements In: *Medical intelligence unit: Retro-vectors for human gene therapy*. (ed. Hodgson, C. P.) 1-51, R.G. Landes Company, Austin, Tex.; 1996).

Adult rat cortex and caudate nucleus were also selected as gene delivery targets. Injection of vector into the rat brain was carried out using a stereotactic head frame with a total dose of $1\times10^8$ pfu/brain. After 3 months AdLTR-luc infection led to markedly higher levels of luciferase in the brain in vivo than the control vector, AdCMV-luc (FIGS. 1D & 1E). The luciferase expression in the AdLTR-luc infected group did not change appreciably by the fourth week, but increased 6- to 13-fold by the eighth and twelfth weeks in both the cortex and the caudate nucleus (~3,101 and 33,755 RLU/25 μg protein at 12 weeks, respectively). In contrast, luciferase expression in the AdCMV-luc infected group was high initially in the cortex (~5,000 RLU/25 μg protein), but was considerably reduced by 8 weeks (~700 RLU/25 μg protein) and did not further change. Many previous studies, in several different tissues, with first generation adenoviral vectors showed considerably shorter terms of transgene expression (Bajocchi et al., *Nature Genetics* 3: 229-234, 1993); Mannes et al., *Brain Res.* 793: 1-6, 1998; Suzuki et al., *Human Gene Therapy* 9, 1223-1231, 1998; Chen et al., *Human Gene Therapy* 8: 341-347, 1997; Gilgenkrantz, H. et al. *Human Gene Therapy* 6: 1265-1274, 1995; Dong et al., *Human Gene Therapy* 7: 319-331, 1996; Yang et al., *Nature Medicine* 9: 890, 1995; Adesanya et al., *Human Gene Therapy* 7: 1085-1093, 1996).

Example 4

Determination of Possible Vector Integration by PCR

Figure 2:
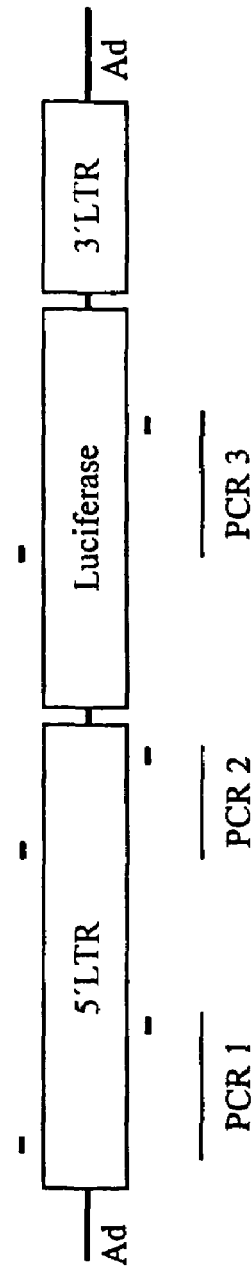
FIG. 2 is a schematic diagram of the location of PCR primers used in a PCR assay for the integration of AdLTR-luc. The primers detect an intact 5'LTR (PCR 1), the downstream 5'LTR (PCR 2) and the luciferase gene (PCR 3) in AdLTR-luc. Target cells or tissues were infected with either AdCMV-luc (AdCMV) or AdLTR-luc (AdLTR).

To screen for the possible integration of the AdLTR-luc vector, a PCR assay was used initially. PCR primers were synthesized in 3 regions of AdLTR-luc (FIG. 2). The amplicon PCR 1 was upstream of the canonical break point, AATG, at the beginning of U3 in the 5'LTR of MoMLV. A second amplicon, PCR 2, was near the 3'end of the 5'LTR, and PCR 3 was amplified from the luciferase gene. Therefore, a result showing PCR 1 to be absent from a cell infected by AdLTR-luc, but PCR 2 and 3 to be present, suggests that integration and breakage of the vector in the 5'LTR occurred. In AdCMV-luc infected cells, PCR 1 and PCR 2 will be negative because there is no LTR sequence present in this control virus. The same template—total cellular DNA—was used for each of the PCR reactions.

In the first experiment, A5 cells were infected with AdCMV-luc or AdLTR-luc and plated to form clones, which were then grown individually. Cell clones that expressed luciferase were selected for further study. The PCR assay of clones infected with AdLTR-luc shows that all clones contained the amplicons PCR 2 and PCR 3. However, the PCR 1 product could not be found in several clones (# 3, #17 and #18), suggesting that at least part of the 5'LTR had been lost. It is important to recognize that clones yielding a PCR 1 amplicon may represent cells infected with both integrated and epichromosomal vectors. The latter would be detected even if integration occurred. In all, 15.5% of the A5 clones infected with AdLTR-luc alone had lost the PCR 1 amplicon. These data are consistent with the hypothesis that AdLTR-luc could mediate integration in vitro in dividing cells. Similar results were seen in HSY and HSG cells.

In vivo, sustained luciferase expression was also related to a loss of the PCR 1 amplicon. PCR assays were performed on tissue isolated from rats at 8, 9, and 12 weeks after infection. For example, the liver, submandibular gland, spleen, brain cortex and caudate nucleus, bone marrow, and peripheral blood were analyzed. By 8-12 weeks post infection, the PCR 1 product could not be amplified from the livers of all 3 animals that received AdLTR-luc, from 2 submandibular glands, from 2 spleens, from 3 brain cortex samples and 3 caudate nuclei. In addition, the 5 end of the vector was undetectable in the bone marrow or peripheral blood of the 3 animals examined at 12 weeks post infection, though the remainder of the vector appeared to be intact. Given that most hematopoietic cells have short half-lives, the persistence of vector in bone marrow and peripheral blood is suggestive of stable integration of the vector. The PCR 3 amplicon was detected in all cloned cells and most tissue samples after AdCMV-luc infection.

Example 5

Determination of Vector Integration by Southern Hybridization

To further examine the apparent integration of AdLTR-luc, Southern hybridization was carried out on DNA samples from A5 cells. Separate studies demonstrated that A5 cells do not exhibit any endogenous reverse transcriptase activity. The A5 cells were infected by either AdLTR-luc or AdCMV-luc and cloned 10 days post infection. Luciferase activity was found in 18 out of 22 AdLTR-luc infected cell clones and 16 out of 24 AdCMV-luc infected clones. The genomic DNA from selected luciferase expressing clones was digested or not by several restriction endonucleases and probed with a 615 bp Hind III/EcoR I fragment from the 5'end of the luciferase cDNA.

Uncut DNA, from both AdLTR-luc and AdCMV-luc infected cells exhibited a single similar band migrating at a position ~37 kb. When DNA was digested with Bam HI plus Not I, all virus-infected samples yielded a single primary band ~2.7 kb, corresponding to the entire luciferase cDNA. DNA samples were next digested with either Sma I or Kpn I. There is one Sma I in each LTR and 13 sites in the adenoviral backbone. There are 3 Kpn I sites in the 5'LTR, one Kpn I site in the 3'LTR, and 10 sites in the adenoviral backbone. Neither enzyme is active within the luciferase cDNA. For DNA prepared from AdCMV-luc infected cells a single positive band was observed with each cloned cell sample. This band was comparable to the single band seen in the positive control sample (uncloned AdCMV-luc cells infected for 2 days). Conversely, with DNA samples from cloned AdLTR-luc infected cells, differences in band size were seen compared to the positive control (P, uncloned AdLTR-luc infected cells, 2 days after infection). For Sma I treated samples, DNA from clones 10 and 11 showed larger positive bands (~9 and 6 kb, respectively), while after Kpn I treatment clone 11 exhibited a larger positive band (over 12 kb). These results are consistent with integration of AdLTR-luc into genomic DNA in these clones.

Finally, DNA samples were treated with either Xho I or Bgl I. Neither of these two enzymes has a restriction site within the LTRs or luciferase cDNA. There are 17 Bgl I sites, and 6 Xho I sites, within the adenoviral backbone. All samples from AdCMV-luc infected cells, including that from the uncloned cells, 2 days post-infection, resulted in a single, identical positive band (~5 and 4 kb, for Xho I and Bgl I, respectively) on hybridization. This was not the case, however, with AdLTR-luc infected samples. All three cell clones tested showed different sized bands from that seen with the positive control DNA (uncloned cells, 2 days post-infection).

These results suggest that the AdLTR-luc vector was able to integrate into genomic DNA and that vector breakpoints were within the 5'LTR sequence. Note that the Sma I site is located at base pair 1714 in the 5'LTR, while the Kpn I sites are at base pairs 260, 443 and 1720 in the 5'LTR. The Sma I and Kpn I digests suggest that the breakpoint in the 5'LTR is likely located downstream of base pair 1720, a finding generally consistent with PCR (see Example 4) and gene walking (below) results.

Example 6

Determination of Vector Integration by FISH

In order to directly investigate the integration of AdLTR-luc, fluorescence in situ hybridization (FISH) was performed on mitotic cells. As hypothesized, no integration of the control vector, AdCMV-luc, was seen in infected HSY cells. In contrast to the finding with AdCMV-luc, there was frequent integration by AdLTR-luc. In HSY and A5 cells the percentage of infected cells with AdLTR-luc integration was 15%. HSY cells demonstrated several copies of the integrated vector. Five percent of spleen lymphocytes from intravenous infected animals were also positive for vector integration by FISH. To assess whether all or part of the AdLTR-luc was integrated into the genome, a two probe hybridization was carried out. The first probe had the 5' and 3'LTR and luciferase sequences. The second probe was from the E4 region of Ad5 (Hind Emi fragment from 30,697 to 36,143 of the plasmid pJM17). These two probes are separated by 30 kb in AdLTR-luc. The integrated vector sequences hybridized to the first probe only, suggesting that integration occurred between the 5' and 3'LTR sequences. When we switched the probe labels and repeated the FISH analysis, only positive hybridization to the first probe was seen.

The pattern of AdLTR-luc insertion into the genome was random: integration was observed in human chromosomes 22, 8, 10 and 2. The FISH data provide direct evidence for the integration of AdLTR-luc in dividing cells in vitro and in vivo and are generally consistent with the results of the PCR and Southern assays (see FIG. 2 for assay design). In particular, it is important to recall that the high frequency of detection of the luciferase gene in cells in vitro (amplicon 3) by PCR is likely due to the presence of non-integrated, epichromosomally-localized virus. The absence of PCR amplicon 1 was noted in A5 cells, however, at a frequency similar to that found for positive integration by FISH in these cells (~15%).

Example 7

Sequencing of Vector Integration Site

Figure 3:
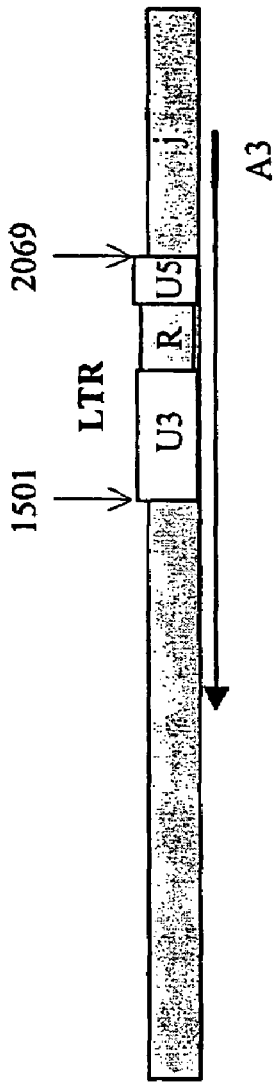
FIG. 3 is a schematic diagram of the sequence of vector-genomic DNA junctions showing the position of the first primer (A3) used for gene walking. The macrophages, mononuclear cells and HSY cell clones were all infected with AdLTR-luc.

In the wild type MoMLV an AATG sequence near the 5' end of the LTR is recognized, two bases (AA) are excised and the virus integrates at this point (see Brown, Integration, in *Retroviruses*. (eds. Coffin, J. M., Hughes, S. H. and Varmus, H. E.) 161-203, Cold Spring Harbor Laboratory Press, Danvers, 1997; Colicelli and Goff, *Cell* 42: 573-580, 1985; Panganiban and Temin, *Nature* 306, 155-160, 1983; Goff, *Annu. Rev. Genet.* 26: 527-544, 1992; Roth et al., *Cell* 58: 47-54, 1989). Therefore, gene walking was used to sequence the junctions of the presumptive 5'LTR breakpoints in cells infected with AdLTR-luc (see Example 2 for the Experimental Protocol). The antisense primer (A3) was located downstream of the 5'LTR, in the packaging signal sequence of MoMLV (FIG. 3). DNA samples used were from macrophages and mononuclear cells (non-dividing cells) and from HSY cells (dividing cells), all infected with AdLTR-luc. Results show that hybrid junction sequences were isolated from all three cell types. Several hundred base pairs of 5'LTR sequence were identified, and non-viral sequences including both known (human PAC, human hypocretin [orexin] receptor, and human BAC) and unknown fragments ranging from several base pairs to more than 240 base pairs were found upstream of the break point. All hybrid junctions found included the potential breakpoint in the 5'LTR between base pairs 1557 and 1961.

These data confirm that AdLTR-luc can integrate into the genomic DNA of non-dividing and dividing cells. The vector was not integrated at the AATG motif, as would be expected for MoMLV. The vector sequence pattern at the break points observed was TC, TT, CC, GG or CT in the macrophages, AC, CC, GA, GC, GT or CG in the mononuclear cells, and GGG, GGT, GGC or ACCC in the HSY cells. The heterogeneity of the break points, and the observation that integration occurred without exogenous integrase, suggest that an atypical process is involved.

Classically (Brown, Integration, In *Retroviruses* (eds. Coffin, J. M., Hughes, S. H. and Varmus, H. E.) 161-203, Cold Spring Harbor Laboratory Press, Danvers, 1997), retroviral integration into the host cell genome requires cis elements (5' and 3'LTR sequences) (see Colicelli and Goff, *Cell* 42: 573-580, 1985; Panganiban, and Temin, *Proc. Natl. Acad. Sci. USA.* 81: 7885-7889, 1984) and virally-encoded integrase (Donehower and Varmus, *Proc. Natl. Acad. Sci. USA* 81: 6461-6465, 1984; Schwartzberg et al., *Cell* 37, 1043-1052, 1984). However, these requirements may not be absolute. For example, mutations in one terminus of the MoMLV genome does not prevent integration of the viral DNA, albeit in an unusual manner, even though the terminal bases were disrupted (Colicelli and Goff, *Cell* 42: 573-580, 1985). There are also suggestions that unintegrated viral DNA can become integrated at low frequency in the absence of integrase (Hagino-Yamagishi et al, *J. Virol.* 61: 1964-1971, 1987; Murphy and Goff, *J. Virol.* 66: 5092-5095, 1992). Furthermore, host cellular proteins (Daniel et al., *Science* 284: 644-647, 1999; Roe et al., *J. Virol.* 71: 1334-1340, 1997; Lee and Craigie, *Proc. Natl. Acad. Sci. USA* 91: 9823-9827, 1994), as well as the manner in which the target DNA is presented (Muller and Varmus, *EMBO J.* 66: 5092-5095, 1992), influence the retroviral integration process. In the present study all of the break points were located in a 404 bp region of the 5'LTR, which suggests a particular role for this retroviral element.

A modified adenovirus has thus been developed that has the ability to integrate into genomic DNA and to mediate long term transgene expression. The results described above extend the classical ideas of adenoviral biology. For example, it is well known that adenovirus type 5 integrates only at very low frequency (approximately $10^{-3}$ to $10^{-5}$ per cell) in vitro (Harui et al., *J. Virol.* 73: 6141-6146, 1999). The results described above for AdLTR-luc demonstrate that the use of a novel hybrid adenoviral results in more frequent genomic integration after adding specific retroviral (e.g. MoMLV LTR) sequences. Also, with the AdLTR-luc vector, the breakpoint of the 5'LTR after integration is not the classical AATG, and cis integrase activity is not necessary for the integration event. The data were derived from multiple experimental approaches, all of which strongly support the conclusion that the hybrid vector AdLTR-luc (FIG. 4) can integrate into genomic DNA much more frequently, and express much longer, than a conventional adenoviral vectors.

Other groups have used an adeno-retrovirus hybrids to improve the efficiency of retroviral vector production (Feng et al., *Nature Biotechnol.* 15: 866-870, 1997; Caplen et al., *Gene Therapy* 6: 454-459, 1999; Ramsey et al, *Biochem. Biophys. Res. Commun* 246: 912-919, 1998; Torrent et al., Abstract #515 presented at 1st Annual Meeting American Society of Gene Therapy, Seattle, Wash., 28 May 1998; Vile, R. G. et al. Abstract #521 presented at 1st Annual Meeting American Society of Gene Therapy, Seattle, Wash., 28 May 1998). In these studies, adenoviruses were constructed to encode the retroviral gag, pol and env sequences. Such viruses, thus, direct the expression of proteins critical for retroviral production and demonstrate that adenovirus-mediated provision of transcomplementing functions can support production of a second (retroviral) vector.

The studies by Feng et al. (supra) and Caplen et al (supra) demonstrate that a similar strategy can be used in vivo. However, these strategies obtain retroviral production as well as proviral integration. In addition, both of these studies only employ nude mouse tumor models versus native tissues as demonstrated herein. Also, both of these earlier studies required the simultaneous administration of multiple transcomplementing viruses versus the single vector utilized in the present report. Furthermore, the hybrid adenoviral vectors of the invention do not encode sequences for any protein needed for retroviral production.

Example 8

Integration of Hybrid Adenoviral Vectors Involves the 5' and the 3' LTRs

The following methods were used to analyze the integration of hybrid adenoviral vectors:

Recombinant Viral Vectors

Vectors used in these experiments are described in Example 1.

Cell Culture

The A5 epithelial cell line was derived from a rat submandibular gland (Brown, *J. Oral Pathol. Med.* 18: 206-213, 1989) and grown in McCoy's 5A medium. A5 cells were infected with AdLTR-luc at 50 pfu/cell. One week later the infected A5 cells were cultured at very low cell density to form single clones on the bottom of a tissue culture dish. Isolated clones were harvested using a glass cylinder 0.5 cm in diameter. Luciferase activity was used to screen clones, and two luciferase positive clones (#10 and 11) were selected for further study (Zheng et al., *Nature Biotechnol.* 18: 176-180, 2000).

Southern Hybridization Analyses

Southern blots were performed as described in Example 1. These blots were hybridized with an [$\alpha$-$^{32}$P] dCTP radiolabelled luciferase probe (a 540 bp Eco RI/Xba I fragment from the 5'end of the luciferase cDNA) and autoradiographed. In this study, the positive control samples used were from A5 cells two days after infection with AdLTR-luc. The negative control samples were obtained from uninfected A5 cells.

PCR Assays

The genomic DNA used for the PCR assays was extracted with a Non-Organic DNA Extraction kit (Intergen). Positive DNA control samples were from A5 cells 2 days post infection with AdLTR-luc. Genomic DNA from the two A5 infected cell clones (#10 and 11) were from the same samples as used in Southern hybridizations. Negative controls used either water alone or genomic DNA from non-infected A5 cells. PCR sensitivity was determined by using 0.5, 5, 50 and 500 ng AdLTR-luc positive control DNA as template. For individual PCR assays with genomic DNA from the infected, cloned A5 cells, 0.5 μg, 3 μg and 10 μg template DNA were used. Taq DNA polymerase was obtained from GIBCO BRL (Rockville, Md.). The primers 3)'LTRf1 (5'-AAGAACA-GATGGTCCCCAGATGCG-3', SEQ ID NO:9) and E2Bb1 (5'-AAGCCACGCCCACACATTTC-3', SEQ ID NO:10) produced the amplicon PCR 1 (1132 bp). The PCR 2 amplicon (786 bp) was amplified by 3'LTRf2 (5'-AACCCTCTTG-CAGTTGCATCC-3', SEQ ID NO:11) and E2Bb2 (5'-GGAACGGGGTGTTTGACATGAC-3', SEQ ID NO:12). The PCR 3 amplicon (888 bp) was amplified by 3'LTRf2 and E2Bb1.

Assessment of Luciferase cDNA Integrity

Figure 12A:
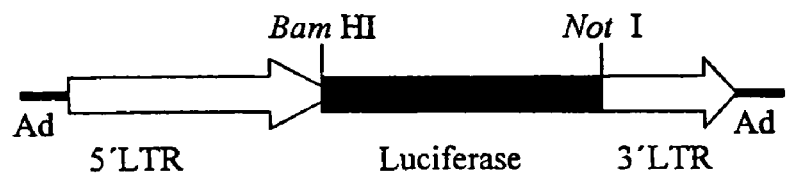
FIG. 12A shows the restriction sites of Bam HI and Not I in AdLTR-luc.

Initially, Southern hybridization with the luciferase probe was carried out on enzyme digested DNA samples from the two A5 cell clones studied, #110 and 11. Bam HI/Not I digestion of AdLTR-luc results in a 2.7 kb band that includes the entire luciferase cDNA (FIG. 12A). Digested genomic DNA from both cloned cells had the same 2.7 kb band as the positive control, indicating the presence of an intact luciferase cDNA.

Determination of Vector Integration in A5 Cell Clones

Figure 12B:
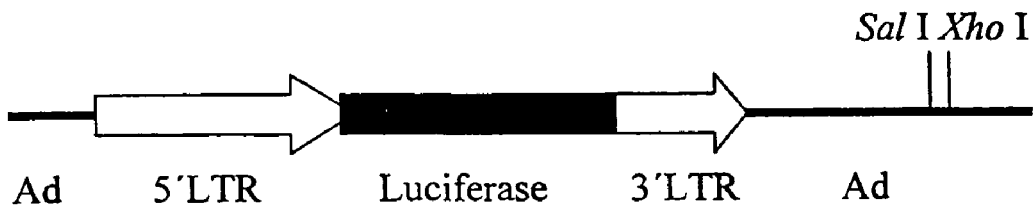
FIG. 12 is a series of schematic diagrams of AdLTR-luc showing the location of restriction sites and a PCR design to detect the 3' LTR break.
FIG. 12C is a partial diagram of Bgl I and Nco I enzyme target sites in AdLTR-luc.
FIG. 12D is a partial diagram of Not1 enzyme target sites in AdLTR-luc.
FIG. 12F is a diagram showing the design of PCR primers used to amplify the junction between the 3'LTR and the E2B region (PCR 1, 2 and 3) in AdLTR-luc.

To screen for AdLTR-luc integration, two restriction endonucleases, Xho I and Sal I, were used to digest DNA samples from the A5 cell clones. There are six Xho I sites, and three Sal I sites in AdLTR-luc. The first Xho I and Sal I sites from the 5'end of AdLTR-luc are located in the adenoviral E2 region (FIG. 12B). Therefore, if integration occurs at a location 5' to these sites, Southern hybridization would yield bands of different size from that seen with the positive control samples (smaller or larger than the positive control depending on Xho I and Sal I restriction endonuclease sites in the genome). Results showed that both clones had hybridization-positive bands different in size compared to the positive control samples. Although these enzyme digestions showed that integration had occurred, the results could not clarify whether there was a break in the 5' and/or 3'LTRs of AdLTR-luc.

Assessment of Possible Breakpoints in the LTRs

Figure 12C:
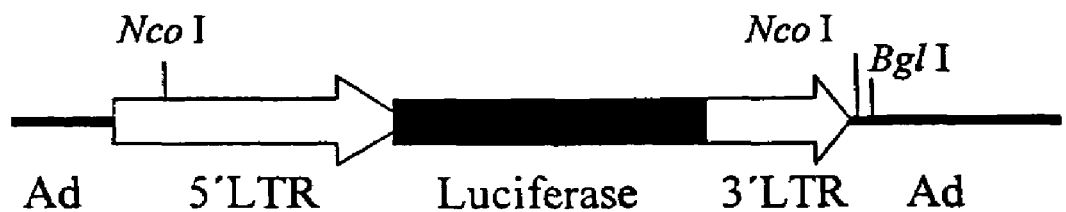

To generally assess if break points were located in the 5' and/or 3'LTRs, Bgl I and Nco I, were used to digest all DNA samples. There is a Bgl I site, and a Nco I site, near the 3'end of the 3'LTR in adenoviral genomic sequence. The Bgl I site is 939 bp downstream of the 3'end of the 3'LTR, while the Nco I site is 336 bp is downstream of the 3'end of the 3'LTR. There is also a Nco I site at nt 647 of the 5'LTR (FIG. 12C). If integration occurred, the Southern hybridizations of samples digested by these two restriction endonucleases would include hybridized bands of different size from that seen in the positive control. The results indicate that there is likely a break in either, or both, of the LTR sequences of AdLTR-luc. Both cell clones demonstrated band sizes different from the positive control samples.

Demonstration of the 5 LTR Break Point

Figure 12D:
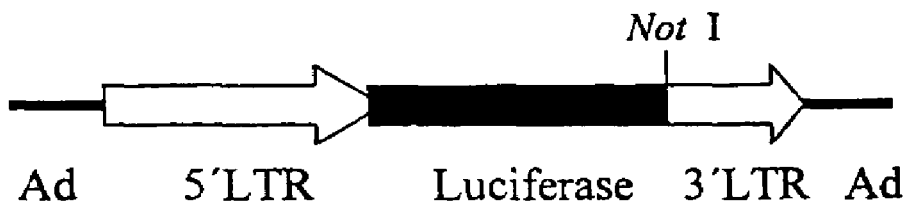

A gene walking assay has been used to demonstrate that there was a break in the 5'LTR (see above). This result was confirmed by Southern hybridization of A5 cell genomic DNA samples digested with Not I. The first Not I site encountered from the 5'end of AdLTR-luc is located between the luciferase cDNA and the 3'LTR (FIG. 12D). No Not I sites are found in the 5'LTR. In addition, there are only 454 bp of adenoviral sequence upstream of the 5'LTR. Therefore, if the results of a Southern hybridization with the luciferase probe after digestion of genomic DNA with Not I indicate bands different in size from the positive control, integration must have occurred within the 5'LTR. Results obtained from Not I digested samples demonstrated that both A5 cell clones had different hybridization band sizes from the positive control sample.

Assessment of Possible 3'LTR Break Points by Southern Hybridization

Figure 12E:
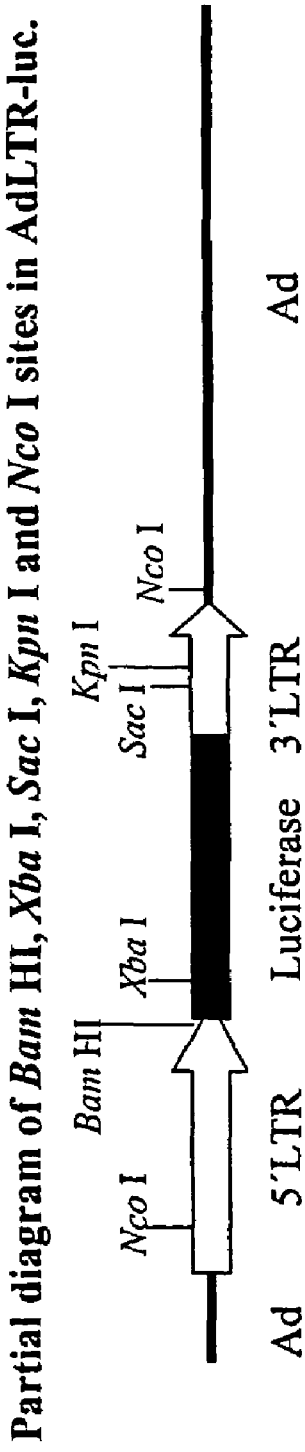

To determine if there was also a break in the 3'LTR, digestions with three pairs of restriction endonucleases were used (see FIG. 12E). The experimental strategy was based on the presence of an intact luciferase cDNA, known from the results described previously. There is a Xba I site in the luciferase cDNA, which is just upstream of the hybridization site of the luciferase probe. There is a Bam HI site between the 5'LTR and the luciferase cDNA. There are Sac I and Kpn I sites in the 3'LTR. Additionally, there are Nco I sites at nt 647 in the 5'LTR and 336 bp from the 3'end of the 3'LTR in the E2B adenoviral region. After digestion with either Xba I/Kpn I, Bam HI/Sac I or Bam HI/Nco I, clones # 10 and 11 exhibited different band sizes from positive control samples. The differences seen with clone # 11 are particularly clear with all digestions. Hybridization bands seen from Clone # 10 were slightly smaller than that of the positive control sample after Xba I/Kpn I and Bam HI/Nco I digestions, and slightly larger than that of the positive control samples after Bam HI/Sac I. The results with both clones #10 and 11 indicate that there is a break in the 3'LTR of AdLTR-luc.

Assessment of Possible 3'LTR Break Points by PCR

Figure 12F:
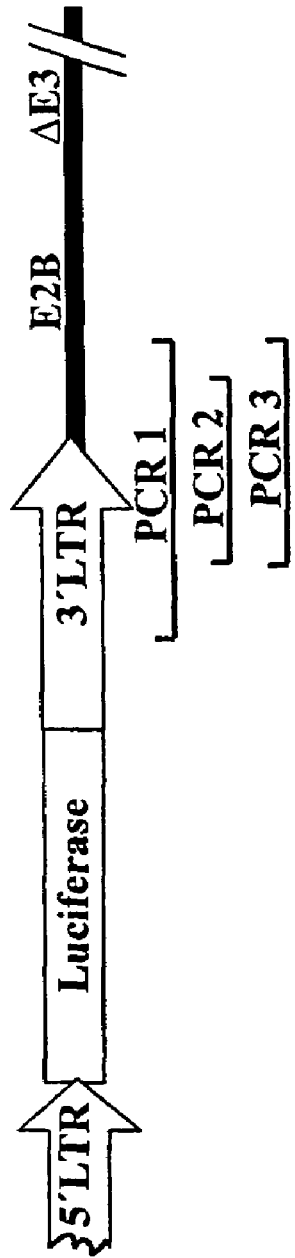

As a separate approach to assess if the 3'LTR was broken during integration, a PCR assay was used. PCR primers were synthesized to yield amplicons within the 3'LTR and the E2B region of AdLTR-luc (FIG. 12F). Amplicons, PCR 1 (1132 bp), 2 (786 bp) and 3 (888 bp), were designed to amplify the junction between the 3'LTR and E2B. An assay for PCR reaction sensitivity showed that all three amplicons were clearly detectable when the template DNA from the AdLTR-luc positive control was decreased to 5 ng/reaction. However, when 0.5 ng template DNA per reaction was used, amplicons PCR 1, 2 and 3 were barely detected. Negative control experiments showed that all three PCR amplicons could not be detected in the non-infected A5 cell genomic DNA samples. The results show that amplicons, PCR 1, 2 and 3 could not be amplified even when ten μg template genomic DNA from clone #10 or 11 was present in each reaction (20-fold higher than maximum of positive control samples; also, two-thirds that used in Southern hybridization analyses). The failure to amplify PCR 1, 2 and 3 from clone #10 and 11 samples is consistent with the occurrence of a break in the 3'LTR during integration.

Thus, a series of Southern hybridization analyses was performed to determine if the integration event seen following infection of cells with AdLTR-luc involved breaks in both the 5' and 3'LTRs. Data from Bam HI/Not I digestions initially showed that both cell clones studied had an intact luciferase cDNA (FIG. 12A). Second, individual digestions with Xho I and Sal I showed that integration occurred in both A5 cell clones (FIG. 12B). Results with Bgl I and Nco I digestions suggested that, indeed, there was a break in either (or both) the 5' or (and) 3'LTRs (FIG. 12C). Next, Not I digestion was used to show that there was a break in 5'LTR of AdLTR-luc in each cell clone (FIG. 12D). Three pairs of restriction endonucleases (Xba I/Kpn I, Bam HI/Sac I, or Bam HI/Nco I) were then used to digest cloned cell genomic DNA samples to test for a break point in the 3'LTR (FIG. 12E). The results indicated that a break in the 3'LTR of AdLTR-luc also occurred.

Finally, as a separate experimental approach to test for the apparent break point in the 3'LTR, three sets of PCR primers were designed to amplify the junction between the 3'LTR and the adenoviral E2B region (FIG. 12F). Despite using as much as 10 μg genomic DNA in each PCR reaction, there was no detection of any of the three amplicons in this assay. These data, although negative, further support the notion that there was a break within the 3'LTR during the integration event. Thus, the demonstration of a break in the 3'LTR in this report is novel, but in keeping with the important role of both LTRs in normal retroviral integration.

Clearly, AdLTR-luc retains some characteristics of MoMLV; AdLTR-luc integrates into the genome, and there are break points in both LTRs. However, classically, retroviral integration into the host cell's genome requires the 5' and 3'LTRs along with virally encoded integrase. The integration of AdLTR-luc integration without viral integrase is particularly unusual. There was no retroviral contamination of, or generation in, the target cell lines used, as tested by reverse transcriptase assays. Despite the absence of MoMLV integrase, integration occurred with the LTR sequences apparently mediating the event. The break point localized in the 5'LTR is not at the classically recognized site (AATG) of MoMLV.

Thus, AdLTR-luc achieved genomic integration and the break points for integration occurred within both the 5' and 3'LTR regions. Without being bound by theory, it appears that both LTR elements play a major role in the integration event for this hybrid vector.

Example 9

The Use of a Hybrid Adenoviral Vector to Introduce HSV-Thymidine Kinase in a Salivary Graft Cell Line Approximately 40,000 new cases of head and neck cancer occur each year in the United States, with about 500,000 new cases worldwide (Vokes et al., *N. Engl. J. Med.* 328:184, 1993). In industrialized countries, the vast majority of these patients receive irradiation treatment. The salivary glands are often included in the radiation field. If the irradiation treatment exceeds ~50 Gy, generally irreversible damage occurs to the salivary glands (Taylor et al., *Proc. Soc. Exp. Biol. Med.*, 221:14, 1999). Irradiation results primarily in the destruction of the fluid secreting acinar cells, and in many individuals all salivary epithelial cells are replaced by nonsecretory tissue (Kashima et al., *Am. J. Roentgenol Radium Ther. Nucl. Med.*, 94:77, 1965). There is no effective conventional therapy for this condition.

A system has been developed consists of a blind end tube fabricated from a biodegradable polymer, coated with a suitable extracellular matrix protein, and lined on its lumen by a monolayer of epithelial cells capable of unidirectional fluid transport (Baum et al., *Ann. N.Y. Acad. Sci.*, 875:294, 1999). An allogeneic graft cell, the HSG cell line, has been used in this system as a model for feasibility studies (Aframian et al., *Tissue Engin.* 6:209, 2000). These cells are derived from a human submandibular gland (Shirasuna et al., *Cancer* 48:745, 1981), and have been widely employed in physiological studies in vitro. HSG cells exhibit functionally coupled neurotransmitter receptors, intact $Ca^{2+}$ signaling systems and various ion channels and transporters important for fluid secretion (Ship et al., *Am. J. Physiol.*, 259:C340, 1990; Kaplan et al., *Pflugers Arch.*, 428:439, 1994; Liu et al., *J. Biol. Chem.* 273:33295, 1998; Izutsu et al., *Am. J. Physiol.*, 266: C58, 1994). Additionally, HSG cells respond to extracellular matrix signals that can direct morphological and tissue-specific differentiation (Royce et al., *Differentiation*, 52:247, 1993; Hoffman et al., *J. Biol. Chem.*, 273:28633, 1998; Lafrenie et al., *Ann. N.Y. Acad. Sci.*, 842:42, 1998). HSG cells seeded on poly-L-lactic acid coated with human fibronectin resulted in maximal cell growth and organization as a monolayer with a cobblestone, epithelioid appearance (Aframian et al., *Tissue Engin.* 6:209, 2000).

However, as a cell line, HSG cells possess unlimited growth potential. Although an artificial gland device could be easily removed from patients in the event of any untoward host response, an additional level of patient safety can be incorporated to eliminate any residual cells after removal of the implant by including a suicide gene into the HSG cells. In one embodiment, this gene is the herpes simplex virus thymidine kinase (HSV-tk) gene.

The HSV-tk gene, in combination with the prodrug ganciclovir (GCV), has been widely employed. GCV is a nucleoside analog that is converted to a monophosphate form in the cell by HSV-tk and then further phosphorylated by host cellular kinases to the triphosphate form, which blocks DNA elongation and results in cell death (Boucher et al., *Hum. Gene Ther.*, 10:801, 1998). By expressing HSV-tk HSG cells could be eliminated by the administration GCV. Thus, HSG cells were transduced with a hybrid recombinant adenoviral vector containing the HSV-tk gene, and the cells were made sensitive to GCV, as described below.

Vectors

Figure 13:
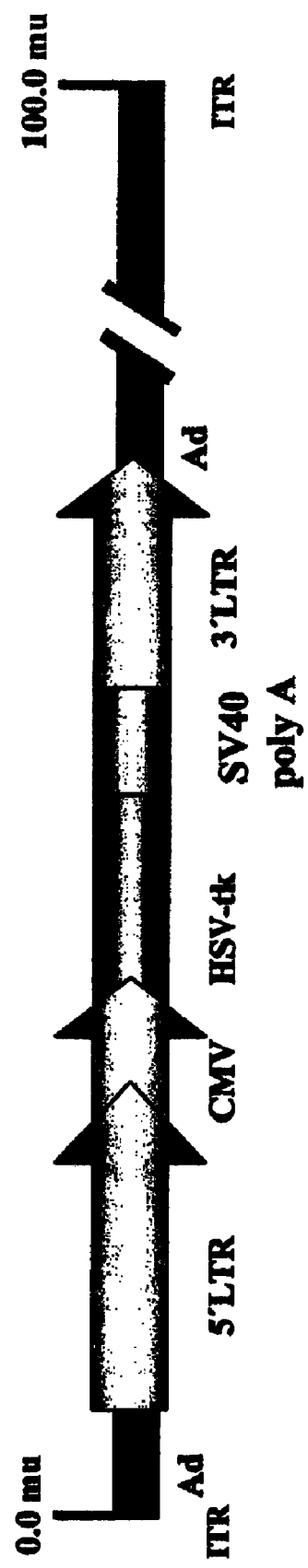
FIG. 13 is a schematic diagram of AdLTR.CMV-tk.

Approximately 2.7 kb of the 5' long terminal repeat (LTR) was removed, which includes part of the envelope gene [1.5 kb], the 5'LTR [0.57 kb], and the packaging sequence [0.63 kb]), and 1 kb of the 3'LTR (which contains about 0.5 kb of the envelope gene and the intact 3'LTR) of the Molony murine leukemia virus from the plasmid pXT1 (Stratagene, La Jolla, Calif.) by digestion with Eco RI (Boulter et al., *Nucleic Acids Res.*, 15:7194, 1987). Sal I linkers were added to both ends of the 5'LTR fragment, and the 3'LTR fragment was filled in to form blunt ends. These two fragments were ligated into pAC-CMV-pLpA (a generous gift of Dr. C. Newgard, University of Texas-Southwestern) from which the CMV promoter/enhancer and the SV40 polyadenylation sequence had been deleted. Thereafter, the CMV promoter/enhancer and the SV40 polyadenylation sequence were reinserted between the 5' and 3'LTRs using Bgl II and Bam HI sites. This created the plasmid pAC5'3'LTR.CMV. A unique Bam HI site remained that could be used to insert the gene of interest. This plasmid was linearized by Bam HI digestion and treated with Klenow fragment to form blunt ends. The 1149 bp HSV-tk cDNA was excised from the plasmid pbTK (a generous gift of Dr. F. Candotti, NHGR1, NIH) by Bam HI and Eco RI, and filled in with Klenow fragment to form blunt ends. The excised HSV-tk cDNA was then cloned into pAC5'3'LTR.CMV to create the plasmid pAC5'3'LTR.CMV-tk. Restriction analysis and DNA sequencing verified the plasmid construction. Next, pAC5'3'LTR.CMV-tk was co-transfected into 293 cells with the adenoviral (type 5; E1$^-$, E3$^-$) plasmid pBHG10 to create a replication-deficient recombinant adenoviral vector by homologous recombination (Zheng et al., *Nat. Biotechnol.*, 18:176, 2000 (herein incorporated by reference); Becker et al., *Methods Cell. Biol.*, 43:161, 1994). This hybrid vector, AdLTR.CMV-tk, contains the Moloney murine leulemia virus 5' and 3' LTRs, and the HSV-tk cDNA with the CMV promotor/enhancer and SV40 polyadenylation sequence (FIG. 13).

Cells and Cell Culture

HSG cells were a generous gift from Prof. M. Sato (Tokushima University, Japan) (Shirasuna et al., *Cancer* 48:745, 1981) and were maintained in vitro as previously described (He et al., *Pflugers Arch.*, 36:416, 1990). For the experiments presented herein, HSG cells were dispersed from semi-confluent plates using a solution of Versene 1:5000 in Hanks' balanced salt solution without calcium and magnesium (BioFluids, Rockville Md.). Cells were then resuspended in fresh media consisting of a 1:1 mixture of Eagle's Minimal Essential Medium, (Dulbecco's Modification) and Ham's F-12 supplemented with 2 mM glutamine (BioFluids), 10% fetal calf serum (Hyclone, Logan, Utah), and 100 units/ml penicillin, 100 µg/ml streptomycin and 2.5 µg/ml fungizone (BioFluids).

Infection and Ganciclovir Application

Cells were grown in 96-well culture plates at a density of $1 \times 10^4$ cells/well. After 24 hours cells were infected with AdLTR.CMV-tk at different MOIs (defined as plaque forming units per cell). Six hours after infection, GCV (Cytovene®, Syntex Laboratories, Inc., Palo Alto Calif.) was added to the media at concentrations of 0.5, 5, or 50 µM. After incubation for different time points, the sensitivity of cells to the GCV prodrug was evaluated using two separate methods, assaying either with the tetrazolium salt of 3-(4,5-dimethylthiazol-2-yl)-2,5-diphenyl tetrasodium bromide (MTT assay, Chemicon International Inc., Temecula, Calif.) or direct cell counting after trypan blue staining (Bio-Whittaker, Walkersville, Md.).

Polymer Disk Preparation

Two-dimensional films of poly-L-lactic acid (Boehringer Ingelheim Inc., Winchester, Va.) were produced by melt processing polymer pellets between sheets of aluminum foil using a Carver press at 350° F. to create disks with diameters of 20-25 mm. The disks were sterilized using y-irradiation for ~150 min with a dose of 20,000 Gy.

Cells Growth on Polymer Disks

Disks were gently placed in each well of a 6-well tissue culture plate (Becton Dickinson, Franklin Lakes, N.J.) and immersed in phosphate-buffered saline (PBS; GibcoBRL, Grand Island, N.Y.) for 18 hours with 5 µg/ml fibronectin at 37° C. (Aframian et al., *Tissue Engin.* 6:209, 2000). Thereafter, the coated disks were blocked for 1 hr with bovine serum albumin (Calbiochem-Novabiochem Corp., La Jolla, Calif.) at 37° C. and then gently washed twice with PBS (Aframian et al., op. cit.). Cell suspensions ($1 \times 10^5$ cells; 2 ml/well) were added in complete culture medium and incubated at 37° C. for an additional 18 hours. Thereafter, the medium was discarded, and 10 MOI of virus diluted in PBS was added for an additional 6 hr. Next, GCV diluted in medium was added, and after an additional 125 hr the disks were washed twice in PBS, then stained with 0.2% crystal violet in 20% ethanol for 20 min (Aframian et al., op. cit). The disks were then rinsed twice with PBS and examined under a light microscope using a 10× objective. Three randomly selected photomicrographs were obtained from each specimen using 200 ASA color slide film (Elite chrome, Kodak, Rochester, N.Y.). The slides were scanned to convert them to digital images and, using Adobe Photoshop®, three 200 µm$^2$ regions were randomly chosen from each field, and cell number was determined visually.

Western Blot Analysis of Thymidine Kinase

Infected and non-infected HSG cells were grown for 72 hr in 150 mm tissue culture plates. Thereafter, cells were scraped from the plates and hypotonically lysed with 1 mM NaHCO$_3$ and 1 mM 4-(2-aminoethyl)-benzenesulfonyl fluoride hydrochloride, a serine protease inhibitor (ICN Biomedicals Inc., Aurora, Ohio). The cell lysate was frozen, thawed and vortexed for 3 cycles, and then centrifuged at 1000×g for 20 min. The resulting supernatant was precipitated with 80% ethanol for 17 hr at −20° C. and centrifuged at 16,000×g for 20 min. The resulting pellet was solubilized in double-distilled water, and the protein concentration was determined by the Bio-Rad/Bradford dye-binding protein assay (BioRad Laboratories, Hercules, Calif.). Next, samples were mixed with an equal volume of 2× sample loading buffer and heated at 95° C. for 5 min before loading 25 µg of total protein on a polyacrylamide gel. The samples were resolved by electrophoresis using 12% Tris-HCl precast polyacrylamide gels (Bio-Rad), and the proteins were transferred onto nitrocellulose membranes. Membranes were incubated in 5% nonfat dry milk in supplemented TBS-T (Geno Technology, St. Louis, Mo.; Tris buffered saline-Tween stock with additional 0.1% Tween 20), plus 1% bovine serum albumin, for 1 hr. Thereafter, the membrane was incubated with a 1:250 dilution of mouse monoclonal antibody 10C11 anti-HSV-tk (obtained from Dr. W. Summers, Yale University) for 1 hr at room temperature. The membrane was transferred to a solution containing a 1:500 dilution of anti-mouse-IgG horseradish peroxidase-conjugated antibody solution in TBS-T (Amersham Life Science Inc., Arlington Heights, Ill.), and the incubation was continued for 1 hr. Between each step the membrane was washed twice for 7 min each in fresh supplemented TBS-T and then washed once with TBS-T stock alone. Finally, the membrane was incubated for 3 min in femtoLUCENT Western detection reagent (Geno Technology) and exposed to X-OMAT film (Eastman Kodak, Rochester, N.Y.).

Statistics

Mean values±SEM for various groups were compared using a two-way analysis of variance with a 95% confidence interval.

Thymidine Kinase Production by Infected HSG Cells

In order to verify the production of the HSV-tk protein, HSG cells were infected with AdLTR.CMV-tk at a MOI of 30 for 72 hr. No cytopathic effects were seen in the infected cells (not shown). Western blot analysis of cell extracts clearly showed a single, approximately 40 kDa immunoreactive protein band in samples from the infected cells corresponding to the expected molecular weight of the HSV-tk protein. This protein band was not detectable in extracts from the control, non-infected cells.

Effects of Ganciclovir on HSG Cells Grown on Plastic

To assess the ability of the HSV-tk transgene to function in HSG cells, cell viability was studied on tissue culture plastic using the MTT assay. HSG cells were infected with different vector MOIs, and thereafter incubated with several concentrations of GCV (Candotti et al., *Cancer Gene Ther.*, 7:574, 2000). In the absence of GCV, HSG cells infected with AdLTR.CMV-tk at a MOI of either 1 or 10 grew normally. Cells infected with AdLTR.CMV-tk at a MOI of 100, however, exhibited substantially decreased viability even without GCV exposure. GCV was without effect on uninfected cells or on cells infected with AdLTR.CMV-tk at a MOI of 1. However, cells infected at a MOI of 10 were sensitive to GCV, showing >50% reduced viability at all prodrug concentrations used ($p<0.02$, <0.006, and <0.004 for 0.5, 5 and 50 µM of GCV, respectively) compared to no GCV treatment.

To determine the surviving cell number under these growth conditions on a plastic substrate following GCV treatment, in separate experiments trypan blue staining was used as well as manual cell counting. These results were consistent with the previous observations. Administration of GCV to cells infected with AdLTR.CMV-tk at a MOI of 10 demonstrated a substantial decrease (up to 3 fold) in number of viable cells compared with cells infected with 10 MOI alone ($p<0.02$, 0.0004, 0.001 for 0.5, 5 and 50 µM GCV, respectively). In this specific set of experiments, a modest but significant reduction in cell viability was observed in cells infected with virus at a MOI of 10 in the absence of GCV ($p<0.03$).

Effect of Ganciclovir on HSG Cells Grown on poly-L-lactic Acid Disks

An artificial salivary gland device will have cells grown as a monolayer on a fibronectin-coated poly-L-lactic acid substratum (Aframian et al., *Tissue Engin.* 6:209, 2000), rather than on tissue culture plastic. Therefore, the ability of GCV to elicit HSG cell death when the cells were attached to poly-L-lactic acid disks pre-coated with 5 µg/ml of human fibronectin was determined. Cells infected with AdLTR.CMV-tk (MOI of 10) were quite sensitive to exposure to GCV in a concentration-dependent manner. The GCV effect ranged from 40% cell death at 0.5 µM GCV to 95% cell death when the GCV concentration was 50 µM. HSG cells treated with 50 µM GCV alone appeared normal with a typical epithelioid cobblestone appearance of cell monolayers. Infection of cells with AdLTR.CMV-tk at a MOI of 10, followed by treatment with 50 µM of GCV, resulted in the loss of almost all of the cells from the disk.

Thus, the HSV-tk gene was delived to HSG cells via a replication-deficient recombinant adenoviral vector, AdLTR.CMV-tk, which can direct random genomic integration of the transgene and long-term gene expression into both dividing and non-dividing cells in vitro and in vivo (Zheng et al., *Nat. Biotechnol.*, 18:176, 2000). AdLTR.CMV-tk infection was without effect on HSG cell growth and viability at MOIs≦10. The encoded suicide gene is expressed in HSG cells, but it is essentially functionally latent until GCV administration. GCV, at doses up to 50 µM, does not affect HSG cell growth and viability in the absence of AdLTR.CMV-tk infection. However, it is demonstrated herein that HSG cells expressing thymidine kinase after AdLTR.CMV-tk infection are quite sensitive to GCV, with cell viability reduced as much as 95%. Thus, after infection with a hybrid recombinant adeno-retrovirus capable of long-term expression and encoding HSV-tk, HSG cells are efficiently killed by GCV treatment. This suggests that the AdLTR.CMV-tk vector may be useful to provide an additional measure of safety for the use of allogeneic graft cells in an artificial tissue device.

Example 10

Testing Hybrid Adenoviral Vectors in Disease Models In Vivo

The hybrid adenoviral vectors described in the above examples can be tested for their ability to express a transgene in mouse models which have been generated for various diseases. Mice which are functionally deleted for a gene, are infected with a hybrid adenoviral vector containing a transgene designed to complement the gene deficiency. Mice are then screened for their ability to express the transgene, and the ability of the transgene to correct the phenotypic affect of the gene deletion.

In one embodiment, hybrid adenoviral vector can be introduced into any organism whose genome has been altered by in vitro manipulation of the early embryo or fertilized egg or by any transgenic technology to induce a specific gene knock-out. A gene knock-out is the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. A hybrid adenoviral vector can be introduced, using any method known to one of skill in the art, in order to introduce a nucleic acid sequence into an animal produced by transgenic technology.

In another embodiment, the hybrid adenoviral vectors can be used to transfect a mouse embryo. Transgenic animals can be produced by introducing into embryos (e.g. a single celled embryo) a hybrid adenoviral vector, in a manner such that the polynucleotides are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, viral infection or other means, the transfected cells are then introduced into the embryo, and the embryo then develops into a transgenic animal. In a preferred method, developing embryos are infected with a hybrid adenovirus containing the desired DNA, and transgenic animals produced from the infected embryo.

In one method DNA is injected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature,* 315:680, 1985; Purcel et al., *Science,* 244:1281, 1986; Wagner et al., U.S. Pat. No. 5,175,385; Krimpenfort et al., U.S. Pat. No. 5,175,384, the respective contents of which are incorporated by reference.

The nucleotide sequence of interest can be fused in proper reading frame under the transcriptional and translational control of a promoter to produce a genetic construct. The genetic construct is then amplified, for example, by preparation in a bacterial vector, according to conventional methods. See, for example, the standard work: Sambrook et al., *Molecular Cloning: a Laboratory Manual*, Cold Spring Harbor Press, 1989, the contents of which are incorporated by reference. The amplified construct is thereafter purified for use in producing transgenic animals.

Example 11

Antisense

In one embodiment, a hybrid adenoviral vector includes an antisense molecule as the transgene. In general, the antisense molecule must by able to bind complementarily to the target RNA. Complementary binding occurs when the base of one molecule forms a hydrogen bond with another molecule. Normally the base Adenine (A) is complementary to thymidine (T) and uracil (U), while cytosine (C) is complementary to guanine (G). Therefore, the sequence 5'-TCGT-3' of the antisense molecule will bind to ACUC of the target RNA, or 5'-ACTC-3' of the target DNA. Additionally, in order to be effective, the antisense and sense molecules do not have to be 100% complementary to the target RNA or DNA.

The antisense polynucleotides can vary in length. Generally, a longer complementary region will give rise to a molecule with higher specificity. When the hybrid adenoviral vector is introduced into a host cell, the host cell supplies the necessary components for transcription of the therapeutic antisense molecule.

Catalytic nucleic acid and other oligomeric molecules can be designed which degrade target sequences and included in a hybrid adenoviral vector of the invention. Such catalytic antisense molecules can contain complementary regions that specifically hybridize to the target sequence, and non-complementary regions which typically contain a sequence that gives the molecule its catalytic activity.

A particular type of catalytic nucleic acid antisense molecule is a ribozyme or anti-sense conjugates, which may be used to inhibit gene expression. (e.g. see PCT publication WO 9523225, and Beigelman et al. *Nucl. Acids Res.* 23:4434-4442, 1995). Examples of oligonucleotides with catalytic activity are described in WO 9506764, WO 9011364, and Sarver et al., *Science* 247:1222-1225, 1990.

The relative ability of an oligomer such as a polynucleotide to bind to a complementary strand is compared by determining the melting temperature of a hybridization complex of a polypeptide and its complementary strand. The melting temperature ($T_m$), a characteristic physical property of double helices, denotes the temperature in degrees Centigrade at which 50% helical versus coiled (unhybridized) forms are present. Base stacking, which occurs during hybridization, is accompanied by a reduction in UV absorption (hypochromicity). A reduction in UV absorption indicates a higher $T_m$. The higher the $T_m$ the greater the strength of the binding of the hybridized strands. As close to optimal fidelity of base pairing as possible achieves optimal hybridization of a polynucleotide to its target RNA.

Example 12

Gene Therapy Using Hybrid Adenoviral Vectors

The present invention provides the transfection of cells in vitro and in vivo. The nucleic acids can transfected into cells by packaging the hybrid adenoviral vector in an adenoviral particle. Thus, both dividing and non-dividing cells can be transfected.

In one particular class of embodiments, adenoviral vectors are used in cell transfection procedures for gene therapy. Gene therapy provides methods for combating chronic infectious diseases such as HIV, as well as non-infectious diseases such as cancer and birth defects such as enzyme deficiencies.

A new gene therapy approach for patients using the hybrid adenoviral vectors taught by the present invention, is now made possible. Essentially, cells can be removed from a subject having deletions or mutations of a gene, and then the hybrid adenoviral vectors (which contains the therapeutic transgene) is introduced into the cell. These transfected cells will thereby produce functional transgene protein and can be reintroduced into the patient. Methods described in U.S. Pat. No. 5,162,215 (Bosselman et al.) demonstrate how to detect the presence and expression of a gene of interest in target cells. Methods described in U.S. Pat. No. 5,741,486 (Pathak et al.) teach the use of viral vectors in gene therapy. Such methods can be applied to the hybrid adenoviral vectors of the present invention, for example in gene therapy.

In addition, the hybrid adenoviral vectors can be introduced into a subject in vivo. The scientific and medical procedures required for human cell transfection are now routine procedures. The provision herein of hybrid adenoviral vectors now allows the development of human and non-human gene therapy based upon these procedures.

In some embodiments, the present invention relates to a method of treating patients which underexpress a gene, or in which greater expression of the gene is desired. These methods can be accomplished by introducing a transgene coding for the underexpressed gene into a hybrid adenoviral vector, which is subsequently introduced into the patient.

In some of the foregoing examples, it may only be necessary to introduce the genetic or protein elements into only certain cells or tissues. However, in some instances (i.e. tumors), it may be more therapeutically effective and simple to treat all of the patients cells, or more broadly disseminate the vector, for example by intravascular administration.

The hybrid adenoviral vectors can be administered to the patient by any method which allows the vectors to reach the appropriate cells. These methods include injection, infusion, deposition, implantation, or topical administration. Injections can be intradermal, intratumor, or subcutaneous.

In addition, the hybrid adenoviral vector can be designed to use different promoters to express the transgene. In one embodiment, the retroviral LTR sequence can serve as a promoter for expression of the transgene. Thus, in one example, a therapeutic nucleic acid is placed under the control of the retroviral LTR promoter. In another embodiment, the transgene is operatively linked to a heterologous promoter (e.g. the CMV promoter). In yet another embodiment, the transgene is operatively linked to a tissue specific promoter (e.g. the immunoglobulin promoter), such that the expression of the transgene occurs only in a tissue of interest.

Ex Vivo Transfection of Cells

Ex vivo methods for introducing a hybrid adenoviral vector in a cell in an organism involve transducing the cell ex vivo, and then introducing the cell into the organism. For example, adenoviral particles including adenoviral capsid proteins and a hybrid adenoviral vector of the invention can be used to treat autologous cells isolated from a subject. In one embodiment, the cells are lymphocytes, macrophages or stem cells isolated or cultured from a subject. Alternatively, the cells can be heterologous cells such as those stored in a cell bank (e.g., a blood bank).

In one specific non-limiting example, the cells are T cells. Several techniques are known for isolating T cells. In one method, Ficoll-Hypaque density gradient centrifugation is used to separate PBMC from red blood cells and neutrophils according to established procedures. Cells are washed with modified AIM-V [which consists of AIM-V (GIBCO) with 2 mM glutamine, 10 µg/ml gentamicin sulfate, 50 µg/ml streptomycin) supplemented with 1% fetal bovine serum (FBS)]. Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.). Transduced cells are prepared for reinfusion according to established methods. See, Abrahamsen et al., *J. Clin. Apheresis* 6:48-53, 1991; Carter et al. *J. Clin. Arpheresis* 4:113-117, 1988; Aebersold et al., *J. Immunol. Methods* 112: 1-7, 1988; Muul et al., *J. Immunol. Methods* 101: 171-181, 1987; and Carter et al., *Transfusion* 27:362-365, 1987).

In another embodiment, adenoviral particles including adenoviral capsid proteins and a hybrid adenoviral vector of the invention can be used to treat a heterologous graft which is then transplanted into the subject. For example, a hybrid adenovirus of the invention can be used to infect a heart, which is subsequently transplanted into a subject requiring a heart transplant.

In Vivo Transfection of Cells

Adenoviral particles containing a hybrid adenoviral vector including a transgene encoding a therapeutic protein can be administered directly to the organism for transduction of cells in vivo. Administration is by any of the routes normally used for introducing a molecule into cells. The packaged nucleic acids are administered in any suitable manner, preferably with pharmaceutically acceptable carriers. Suitable methods of administering such packaged nucleic acids in the context of the present invention to a patient are available, and although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Injection solutions and suspensions can be prepared from sterile powders, granules, and tablets of the kind previously described. Cells transduced by the packaged nucleic acid as described above in the context of ex vivo therapy can also be administered intravenously or parenterally as described above. The dose administered to a subject, in the context of the present invention should be sufficient to effect a beneficial therapeutic response in the patient over time, or to inhibit infection by a pathogen. The dose will be determined by the efficacy of the particular transgene employed and the condition of the patient, as well as the body weight or surface area of the subject to be treated. The size of the dose also will be determined by the existence, nature, and extent of any adverse side-effects that accompany the administration of a particular vector, or transduced cell type in a particular patient.

In determining the effective amount of the hybrid adenoviral vector to be administered in the treatment of a disease, the physician or other clinician evaluates symptom or clinical parameters, including the progression of the disease. In general, the dose equivalent of a naked nucleic acid from a vector is from about 1 µg to 100 µg for a typical 70 kilogram. The exact dosage of adenoviral particles including a hybrid adenoviral vector of the invention is dependent upon a variety of factors, including the age, weight, and sex of the subject to be treated, and the nature and extent of the disease or disorder to be treated. Effective doses can be extrapolated from dose-response curves derived from in vitro or animal model test systems.

Administration can be accomplished via single or divided doses. Methods of introduction include, but are not limited to, intradermal, intramuscular, intraperitoneal, intravenous, subcutaneous, intranasal, and oral routes. Administration can be by any convenient route, for example by infusion or bolus injection, by absorption through epithelial or mucocutaneous linings (e.g., oral mucosa, rectal and intestinal mucosa, etc.). In addition, the pharmaceutical compositions can be introduced into the central nervous system by any suitable route, including intraventricular and intrathecal injection; intraventricular injection can be facilitated by an intraventricular catheter, for example, attached to a reservoir, such as an Ommaya reservoir. Administration can be systemic or local. The adenoviral particles of the invention can be administered together with other biologically active agents.

In one embodiment, it may be desirable to administer the pharmaceutical compositions of the invention locally to the area in need of treatment, for example, by local infusion during surgery, topical application, e.g., in conjunction with a wound dressing after surgery, by injection, through a catheter, by a suppository or an implant, such as a porous, non-porous, or gelatinous material, including membranes, such as silastic membranes, or fibers. In one embodiment, administration can be by direct injection at the site (or former site) of a malignant tumor or neoplastic or pre-neoplastic tissue.

The present invention also provides pharmaceutical compositions which include a therapeutically effective amount of the hybrid adenoviral vectors, alone or with a pharmaceutically acceptable carrier.

Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

The pharmaceutical compositions or methods of treatment can be administered in combination with other therapeutic treatments, such as other antineoplastic or antitumorigenic therapies.

Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the present invention are normal saline and sesame oil.

Embodiments of the invention comprising medicaments can be prepared with conventional pharmaceutically acceptable carriers, adjuvants and counterions as would be known to those of skill in the art.

Having illustrated and described the principles of generating a hybrid adenoviral vectors for use in the delivery of transgenes to a cell or subject, the art of the invention can be modified in arrangement and detail without departing from such principles. In view of the many possible embodiments to which the principles of my invention can be applied, it should be recognized that the illustrated embodiments are only examples of the invention and should not be taken as a limitation on the scope of the invention. Rather, the scope of the invention is in accord with the following claims. We therefore claim as our invention all that comes within the scope and spirit of these claims.

REFERENCES

All publications mentioned herein are incorporated herein by reference in full for the purpose of describing and disclosing the adenoviral components, retroviral components, and methodologies which are described in the publications which might be used in connection with the presently described invention. The publications discussed throughout the text are provided solely for their disclosure prior to the filing date of the present application. Nothing herein is to be construed as an admission that the inventor is not entitled to antedate such disclosure by virtue of prior invention.

1. Blaese et al., T lymphocyte-directed gene therapy for ADA-SCID: initial trial results after 4 years, *Science* 270, 475-480 (1995).
2. Anderson, Human gene therapy, *Nature* 392, 25-30 (1998).
3. Crystal, Transfer of gene to humans: Early lessons and obstacles to success, *Science* 270, 404-410(1995).
4. Verma and Somia, Gene therapy-promises, problems and prospects, *Nature* 389, 239-242 (1997).
5. Nabel, Development of optimized vectors for gene therapy, *Proc. Natl. Acad. Sci. USA* 96, 324-326 (1999).
6. Springett et al., Infection efficiency of T lymphocytes with amphotropic retroviral vectors is cell cycle dependent, *J. Virol.* 63, 3865-3869 (1989).
7. Miller et al., Gene transfer by retrovirus vectors occurs only in cells that are actively replicating at the time of infection, *Mol. Cell. Biol.* 10, 4239-4242 (1990).
8. Harel et al., Cell cycle dependence of synthesis of unintegrated viral DNA in mouse cells newly infected with murine leukemia virus, *Virology* 110, 202-207 (1981).
9. Dales and Chardonnet, Early events in the interaction of adenoviruses with HeLa cells, IV. Association with microtubules and the nuclear pore complex during vectorial movement of the inoculum, *Virology* 56, 465-483 (1973).
10. Greber et al., The role of the nuclear pore complex in adenovirus DNA entry, *EMBO J.* 16, 5998-6007 (1997).
11. Greber et al., The role of the adenovirus protease on virus entry into cells, *EMBO J.* 15, 1766-1777 (1996).
12. Schaack et al., Adenovirus terminal protein mediates both nuclear matrix association and efficient transcription of adenovirus DNA, *Genes Dev.* 4, 1197-1208 (1990).
13. Harui et al., Frequency and stability of chromosomal integration of adenovirus vectors, *J. Virol.* 73, 6141-6146 (1999).
14. Feng et al., Stable in vivo gene transduction via a novel adenoviral/retroviral chimeric vector, *Nature Biotechnol.* 15, 866-870 (1997).
15. Caplen et al., Adeno-retroviral chimeric viruses as in vivo transducing agents, *Gene Therapy* 6, 454-459 (1999).
16. Ramsey et al., Adenovirus vectors as transcomplementing templates for the production of replication defective retroviral vectors, *Biochem. Biophys. Res. Commun.* 246, 912-919 (1998).
17. Torrent et al., Induction of retroviral producer cells following delivery of retroviral vector and packaging functions with E1E4-doubly-defective adenoviruses. Abstract #515 presented at $1^{st}$ Annual Meeting American Society of Gene Therapy, Seattle, Wash., 28 May 1998.
18. Vile et al., Adenoviral-mediated delivery of a retroviral provirus retaining only the termini of the LTRs to produce a high titer, integrating vector which infects non-dividing cells. Abstract #521 presented at $1^{st}$ Annual Meeting American Society of Gene Therapy, Seattle, Wash., 28 May 1998.
19. Hodgson, The retroelements In *Medical intelligence unit: Retro-vectors for human gene therapy* (ed. Hodgson, C. P.), 1-51 (R.G. Landes Company, Austin, Tex.; 1996).
20. Bajocchi et al., Direct in vivo gene transfer to ependymal cells in the central nervous system using recombinant adenovirus vectors, *Nature Genetics* 3, 229-234 (1993).
21. Mannes et al., Adenoviral gene transfer to spinal cord neurons: Intrathecal versus intraparenchymal administration, *Brain Res.* 793, 1-6 (1998).
22. Suzuki et al., Similarity of strain- and route-dependent murine responses to an adenovirus vector using the homologous thrombopoietin cDNA as the reporter genes, *Human Gene Therapy* 9, 1223-1231 (1998).
23. Chen et al., Adenovirus-mediated delivery of human kallistatin gene reduces blood pressure of spontaneously hypertensive rats, *Human Gene Therapy* 8, 341-347 (1997).
24. Gilgenkrantz et al., Transient expression of genes transferred in vivo into heart using first-generation adenoviral vectors: role of the immune response, *Human Gene Therapy* 6, 1265-1274 (1995).
25. Dong et al., Systematic analysis of repeated gene delivery into animal lungs with a recombinant adenovirus vector, *Human Gene Therapy* 7, 319-331 (1996).
26. Yang et al., Recombinant IL-12 prevents formation of blocking IgA antibodies to recombinant adenovirus and allows repeated gene therapy to mouse lung, *Nature Medicine* 9, 890—(1995).
27. Adesanya et al., Immediate inflammatory responses to adenovirus-mediated gene transfer in rat salivary glands, *Human Gene Therapy* 7: 1085-1093 (1996).
28. Brown, Integration. In *Retroviruses*, (eds. Coffin, J. M., Hughes, S. H. and Varmus, H. E.) 161-203 (Cold Spring Harbor Laboratory Press, Danvers; 1997).

29. Colicelli and Goff, Mutants and pseudorevertants of Moloney murine leukemia virus with alterations at the integration site, *Cell* 42, 573-580 (1985).
30. Panganiban and Temin, The terminal nucleotides of retrovirus DNA are required for integration but not virus production, *Nature* 306, 155-160 (1983).
31. Goff, Genetics of retroviral integration, *Annu. Rev. Genet.* 26, 527-544 (1992).
32. Roth et al., Structure of the termini of DNA intermediates in the integration of retroviral DNA: dependence on IN function and terminal DNA sequence, *Cell* 58, 47-54 (1989).
33. Asante-Appiah and Skalka, Molecular mechanisms in retrovirus DNA integration, *Antiviral Res.* 36, 139-156 (1997).
34. Panganiban and Temin, The retrovirus pol gene encodes a product required for DNA integration: identification of a retrovirus int locus, *Proc. Natl. Acad. Sci. USA.* 81, 7885-7889 (1984).
35. Donehower and Varmus, A mutant murine leukemia virus with a single missense codon in pol is defective in a function affecting integration, *Proc. Natl. Acad. Sci. USA* 81, 6461-6465 (1984).
36. Schwartzberg et al., Construction and analysis of deletion mutations in the pol gene of Moloney murine leukemia virus: a new viral function required for productive infection, *Cell* 37, 1043-1052 (1984).
37. Hagino-Yamagishi et al., Retroviral DNA integrated during infection by an integration-deficient mutant of murine leukemia virus is oligomeric, *J. Virol.* 61, 1964-1971 (1987).
38. Murphy and Goff, A mutation at one end of Moloney murine leukemia virus DNA blocks cleavage of both ends by the viral integrase in vivo, *J. Virol.* 66, 5092-5095 (1992).
39. Daniel et al., A role for DNA-PK in retroviral DNA integration, *Science* 284, 644-647 (1999).
40. Roe et al., 3'-End processing and kinetics of 5'-end joining during retroviral integration in vivo, *J. Virol.* 71, 1334-1340 (1997).
41. Lee and Craigie, Protection of retroviral DNA from autointegration: Involvement of a cellular factor, *Proc. Natl. Acad. Sci. USA* 91, 9823-9827 (1994).
42. Muller and Varmus, DNA bending creates favored sites for retroviral integration: an explanation for preferred insertion sites in nucleosomes, *EMBO J.* 66, 5092-5095 (1992).
43. Boulter and Wagner, A universal retroviral vector for efficient constitutive expression of exogenous genes, *Nucleic Acids Res.* 15, 7194 (1987)
44. Becker et al., Use of recombinant adenovirus for metabolic engineering of mammalian cells, In *Methods in Cell Biology* (ed. Roth, M. G.) 161-189 (Academic press, San Diego; 1994).
45. Yanagawa et al., Generation of cells with phenotypes of both intercalated duct-type and myoethelial cells in human parotid gland adeocarcinoma clonal cells grown in athymic nude mice, *Virchows Arch. [B]* 51, 1871-1885 (1986).
46. Brown et al., Establishment and characterization of an epithelial cell line from the rat submandibular gland, *J. Oral Pathol. Med.* 18, 206-213 (1989).
47. Shirasuna et al., A neoplastic epithelial duct cell line established from an irradiated human salivary gland, *Cancer* 48, 745-752 (1981).
48. Heng et al., High-resolution mapping of mammalian genes by in situ hybridization to free chromatin, *Proc. Nat. Acad. Sci. USA.* 89, 9509-9513 (1992).

What is claimed is:

1. A method for stably introducing a transgene into a cell in vivo with a single viral vector, comprising:
   contacting the cell with an adenovirus, wherein the adenovirus comprises
   adenoviral capsid proteins; and
   an adenoviral vector comprising
   (a) a 5' retroviral LTR nucleic acid sequence, a 3' retroviral LTR nucleic acid sequence, wherein the 5' and the 3' retroviral LTR nucleic acid sequences are Moloney Leukemia Virus LTR nucleic acid sequences,
   (b) a retroviral nucleic acid sequence comprising a nucleic acid sequence encoding a portion of a retroviral envelope protein adjacent to either the 5' LTR or the 3' LTR nucleic acid sequence, wherein the retroviral nucleic acid sequence does not comprise a nucleic acid sequence encoding a functional retroviral gag or a functional retroviral pol, or both,
   (c) a nucleic acid sequence encoding a transgene located between the 5, LTR and the 3' LTR, wherein the adenoviral vector is replication-defective and has a functional deletion of a nucleic acid sequence encoding an early transcriptional unit polypeptide, thereby introducing the adenoviral vector into the cell,
   wherein the cell is not able to produce viral particles, and wherein no other viral vector is introduced into the cell, thereby stably introducing a transgene into a cell in vivo.

2. The method of claim 1, wherein the adenoviral vector further comprises a promoter operably linked to the transgene.

3. The method of claim 1, wherein the adenoviral vector is integrated into a chromosome of the cell.

4. The method of claim 1, wherein the transgene is a marker polypeptide, an enzyme, or a therapeutic polypeptide.

5. The method of claim 4, wherein the transgene encodes erythropoietin.

6. The method of claim 1, wherein the adenoviral vector further comprises two adenoviral inverted terminal repeats and does not encode early transcriptional unit polypeptides E1 and E3.

7. The method of claim 1, wherein the adenoviral vector is packaged in the adenoviral capsid proteins, thereby producing infective adenovirus.

8. The method of claim 1, wherein the cell is a mammalian cell.

9. The method of claim 1, wherein the functional deletion in the adenoviral vector is a mutation or a deletion of the nucleic acid sequence encoding the early transcriptional unit polypeptide.

10. The method of claim 9, wherein the early transcriptional unit polypeptide is E1.

11. The method of claim 10, wherein the adenoviral vector further comprises a deletion in a nucleic acid sequence encoding an E3 early transcriptional unit polypeptide.

12. The method of claim 1, further comprising a retroviral packaging sequence, and wherein the 5' retroviral LTR nucleic acid sequence, the 3' retroviral LTR nucleic acid sequence, nucleic acid sequence encoding the transgene, the retroviral nucleic acid sequence comprising a nucleic acid sequence encoding the portion of the retroviral envelope polypeptide, and the retroviral packaging sequence are inserted into the nucleic acid sequence encoding the early transcriptional unit polypeptide.

13. The method of claim 2, wherein the promoter is a cytomegalovirus (CMV) promoter.

14. The method of claim 1, wherein the transgene is stably introduced into a non-human cell.

* * * * *

UNITED STATES PATENT AND TRADEMARK OFFICE
CERTIFICATE OF CORRECTION

PATENT NO.       : 7,618,623 B2                                    Page 1 of 1
APPLICATION NO. : 11/255059
DATED            : November 17, 2009
INVENTOR(S)      : Zheng et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 746 days.

Signed and Sealed this

Twenty-sixth Day of October, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 1
tctccaccac catactgaac c          21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 2
tcaaaactag agcctggacc          20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR primer

```
<400> SEQUENCE: 3
tgtggttctg gtaggagacg                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4
ccaacgtctc ttcttgacat                                                20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 5
aggcgaatta tgtgtcagag g                                              21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 6
ttggggtgtt gtaacaata                                                 19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 7
ccaacgtctc ttcttgacat                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 8
gaaacacagt cagacagaga                                                20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 9
aagaacagat ggtccccaga tgcg                                           24

<210> SEQ ID NO 10
<211> LENGTH: 20
```

```
<212> TYPE: DNA
<213> ORGANISM: Artificial Sequence
<220> FEATURE:
<223> OTHER INFORMATION: Description of Artificial Sequence: PCR primer

<400> SEQUENCE: 10
aagccacgcc cacacatttc                                                    20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 11
aaccctcttg cagttgcatc c                                                  21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 12
ggaacggggt gtttgacatg ac                                                 22
```